(12) United States Patent
Sankai et al.

(10) Patent No.: US 8,773,148 B2
(45) Date of Patent: Jul. 8, 2014

(54) CENTROID POSITION DETECTOR DEVICE AND WEARING TYPE ACTION ASSISTANCE DEVICE INCLUDING CENTROID POSITION DETECTOR DEVICE

(75) Inventors: Yoshiyuki Sankai, Tsukuba (JP); Kazuki Into, Tsukuba (JP)

(73) Assignees: University of Tsukuba, Ibaraki (JP); CYBERDYNE Inc., Ibaraki (JP)

( * ) Notice: Subject to any disclaimer, the term of this patent is extended or adjusted under 35 U.S.C. 154(b) by 553 days.

(21) Appl. No.: 12/810,102

(22) PCT Filed: Dec. 9, 2008

(86) PCT No.: PCT/JP2008/072344
§ 371 (c)(1),
(2), (4) Date: Jun. 22, 2010

(87) PCT Pub. No.: WO2009/084387
PCT Pub. Date: Jul. 9, 2009

(65) Prior Publication Data
US 2010/0271051 A1    Oct. 28, 2010

(30) Foreign Application Priority Data

Dec. 27, 2007  (JP) .................................. 2007-337166

(51) Int. Cl.
*G01R 27/26*  (2006.01)

(52) U.S. Cl.
USPC .......................................................... 324/686

(58) Field of Classification Search
CPC ....................................................... G01R 27/26
See application file for complete search history.

(56) References Cited

U.S. PATENT DOCUMENTS

| 3,329,957 A | * | 7/1967 | Hoynes ......................... 343/718 |
| 5,813,142 A | * | 9/1998 | Demon ............................. 36/29 |

(Continued)

FOREIGN PATENT DOCUMENTS

| CN | 1838933 | 9/2006 |
| JP | 63-263422 | 10/1988 |

(Continued)

OTHER PUBLICATIONS

Korean Office Action mailed Aug. 11, 2011.

(Continued)

*Primary Examiner* — Arleen M Vazquez
*Assistant Examiner* — Feba Pothen
(74) *Attorney, Agent, or Firm* — IPUSA, PLLC

(57) ABSTRACT

Load measuring parts 50 and 52 are provided with reaction sensors 50a, 50b, 52a and 52b to measure loads at two positions, the tiptoe and the heel, on each sole of right and left feet of a wearing person 12. The reaction sensor 50a detects a reaction force to a load on a front side of the right foot (right tiptoe), the reaction sensor 50b detects a reaction force to a load on a rear side of the right foot (right heel), the reaction sensor 52a detects a reaction force to a load on a front side of the left foot (left tiptoe), and the reaction sensor 52b detects a reaction force to a load on a rear side of the left foot (left heel). The reaction sensors 50a, 50b, 52a and 52b are arranged to detect, based on a change of a capacitance, the loads on the right and left feet during a walk action. A change of the load accompanied with a shift of the weight and a contact between the wearing person's foot and the ground can be detected.

10 Claims, 22 Drawing Sheets

(56) References Cited

U.S. PATENT DOCUMENTS

| | | | |
|---|---|---|---|
| 7,093,497 B2* | 8/2006 | Takenaka et al. | 73/763 |
| 7,472,028 B2* | 12/2008 | Foote | 702/65 |
| 2006/0162464 A1* | 7/2006 | Hayashi et al. | 73/818 |
| 2006/0211956 A1* | 9/2006 | Sankai | 601/5 |
| 2007/0003915 A1* | 1/2007 | Templeman | 434/247 |
| 2008/0306410 A1* | 12/2008 | Kalpaxis et al. | 600/592 |

FOREIGN PATENT DOCUMENTS

| | | | |
|---|---|---|---|
| JP | 02-069620 | | 3/1990 |
| JP | 02-078925 | | 3/1990 |
| JP | 09-168529 | | 6/1997 |
| JP | 11-083608 A | | 3/1999 |
| JP | 2000180253 | * | 6/2000 |
| JP | 2005-095561 | | 4/2005 |
| JP | 2006-204730 | | 8/2006 |
| JP | 2006-284404 | | 10/2006 |
| JP | 2006-322814 | | 11/2006 |
| KR | 2004-0074097 A | | 8/2004 |
| KR | 2005-0062783 A | | 6/2005 |
| WO | WO03-057420 A1 | | 7/2003 |

OTHER PUBLICATIONS

Chinese Office Action mailed Aug. 26, 2011.

* cited by examiner (Wb > Wa)

CENTROID POSITION DETECTOR DEVICE AND WEARING TYPE ACTION ASSISTANCE DEVICE INCLUDING CENTROID POSITION DETECTOR DEVICE

TECHNICAL FIELD

This invention relates to a centroid position detector device which measures loads on the soles of a wearing person and detects a shift of a position of a center of gravity of the wearing person according to a change of the measured loads, and relates to a wearing type action assistance device including the centroid position detector device.

BACKGROUND ART

A wearing type action assistance device is under development (see Patent Document 1 listed below). For example, when a person has an arm or a leg that does not easily work due to a disease of its joint or the joint does not easily work due to deterioration of a muscular power of the person, the person may wear this wearing type action assistance device by attaching an action assisting tool to the arm or the leg, in order to assist the action of the person around the joint.

This wearing type action assistance device is arranged to detect a myoelectricity signal that takes place according to a wearing person's intention, and arranged to generate a control signal to control a motor of the action assisting tool, based on the detected myoelectricity signal. Hence, the wearing type action assistance device enables a driving force of the action assisting tool to be transmitted to the arm or the leg as if by the wearing person's own muscular power.

When a walk action is performed by the wearing person, an assisting torque (assisting force) by the motor is controlled based on the detected myoelectricity signal as described above, and a position of a center of gravity (centroid position) of the wearing person according to the walk action is detected by measuring a load (weight) acting on the soles of the wearing person. The timing of outputting the assisting torque from the motor is adjusted in accordance with the walking speed of the wearing person and the timing of the alternate motions of the right and right feet. Thereby, the wearing person who receives the assisting torque from the motor is able to walk smoothly as if by the wearing person's own muscular power.

In a centroid position detector device according to the related art, a center-of-gravity sensor (reaction sensor) which detects a position of a center of gravity of a wearing person is attached to each of the soles of the wearing person. Using such sensors, the loads acting on the soles of the right and left feet accompanied with a walk action are detected, and a position of the center of gravity of the wearing person is determined based on changes of the loads on the soles of the right and left feet. As an example of the center-of-gravity sensor, for example, Patent Document 2 listed below discloses a plurality of pressure-sensitive sensors arranged to detect pressures of the weight acting on the right and left feet of a person.

Patent Document 1: Japanese Laid-Open Patent Publication No. 2005-95561
Patent Document 2: Japanese Laid-Open Patent Publication No. 2006-204730

DISCLOSURE OF THE INVENTION

Problem to be Solved by the Invention

However, the centroid position detector device according to the related art uses a pressure-sensitive sensor as the center-of-gravity sensor, which is arranged to detect a pressure (reaction force) of the weight of the wearing person according to a walk action. The weight of the wearing person acts on the pressure-sensitive sensor repeatedly according to the walk action, and a deformation takes place by an action of the sole of the wearing person. A film-like conductive layer formed in the pressure-sensitive sensor is likely to fracture due to the deformation. There is a problem in that the centroid position detector device according to the related art has poor durability.

Accordingly, in an aspect of the invention, the present disclosure provides a centroid position detector device in which one or more of the above-described problems are reduced or eliminated, and a wearing type action assistance device including the centroid position detector device.

Means for Solving the Problem

In embodiments of the invention which solves or reduces one or more of the above-mentioned problems, the present disclosure provides the following:

(1) a centroid position detector device which includes a load measuring part to measure a load on a sole side of a foot of a person and is arranged to detect a position of a center of gravity of the person based on a change of the load measured by the load measuring part, wherein the load measuring part is fitted in contact with the sole side of the foot and arranged to detect a capacitance which varies according to a shift of a weight of the person;

(2) in the centroid position detector device according to (1), the load measuring part is arranged to measure loads at two positions, corresponding to a tiptoe and a heel, on the sole side of the foot;

(3) in the centroid position detector device according to (1), the load measuring part is arranged in an insole of a shoe;

(4) in the centroid position detector device according to (1), the load measuring part includes: a sheet-like elastic plate having elasticity; an upper electrode bonded to a top surface of the elastic plate; and a lower electrode bonded to a bottom surface of the elastic plate, wherein the load measuring part is arranged to detect a capacitance between the upper electrode and the lower electrode;

(5) in the centroid position detector device according to (4), one of the upper and lower electrodes is grounded, the other of the upper and lower electrodes is connected to a constant-voltage power source, and a capacitance is computed based on a time a value of a voltage between the upper electrode and the lower electrode reaches a predetermined value;

(6) in the centroid position detector device according to (1), the load measuring part includes: a lower ground electrode; a lower elastic plate laminated on a top surface of the lower ground electrode; a voltage sensing electrode laminated on a top surface of the lower elastic plate; an upper elastic plate laminated on a top surface of the voltage sensing electrode; and an upper ground electrode laminated on a top surface of the upper elastic plate, wherein the load measuring part is arranged to detect a capacitance based on a time a voltage detected from the voltage sensing electrode reaches a predetermined reference voltage;

(7) in the centroid position detector device according to (6), the load measuring part is arranged so that the lower ground electrode, the lower elastic plate, the voltage sensing electrode, the upper elastic plate, and the upper ground electrode are laminated and bonded together;

(8) in the centroid position detector device according to (1), the load measuring part includes: a first electrode sheet having a plurality of electrode wires arranged in parallel with a first direction at intervals of a predetermined distance; an elastic sheet laminated on a top surface of the first electrode sheet; and a second electrode sheet laminated on a top surface of the elastic sheet and having a plurality of electrode wires arranged in parallel with a second direction at intervals of a predetermined distance, the second direction being not parallel to the first direction, wherein a capacitance is sequentially detected at each of a plurality of points where the electrode wires of the first electrode sheet and the electrode wires of the second electrode sheet intersect each other;

(9) in the centroid position detector device according to (8), the first electrode sheet and the second electrode sheet are formed of a film-like flexible substrate, the elastic sheet is interposed between the first electrode sheet and the second electrode sheet, and the first electrode sheet, the elastic sheet, and the second electrode sheet are laminated and bonded together;

(10) a wearing type action assistance device including: the centroid position detector device according to (1); an actuator to generate an action assisting force; a frame to transmit a driving force of the actuator to the foot of the wearing person; a biosignal detecting part to detect a biosignal from the wearing person accompanied with a walk action of the wearing person; and a control unit to control the driving force of the actuator based on the biosignal detected by the biosignal detecting part and the position of the center of gravity detected by the centroid position detector device; and

(11) in the wearing type action assistance device according to (10), the centroid position detector device further includes: a first load measuring part to measure a right foot load acting on a bottom surface of a right foot of the wearing person; a second load measuring part to measure a left foot load acting on a bottom surface of a left foot of the wearing person; and a detecting part to detect a position of the center of gravity of the wearing person based on a rate of the right foot load measured by the first load measuring part and the left foot load measured by the second load measuring part.

Effects of the Invention

According to the present disclosure, a change of a capacitance according to a shift of the weight of a wearing person is detected and a shift of a position of the center of gravity of the wearing person is detected. The capacitance according to the loads on the soles of the wearing person can be detected even if some of the electrodes are damaged. It is possible to detect a position of the center of gravity even if a deformation takes place repeatedly by an action of the wearing person, and it is possible to remarkably increase the durability of the centroid position detector device.

Figure 1:
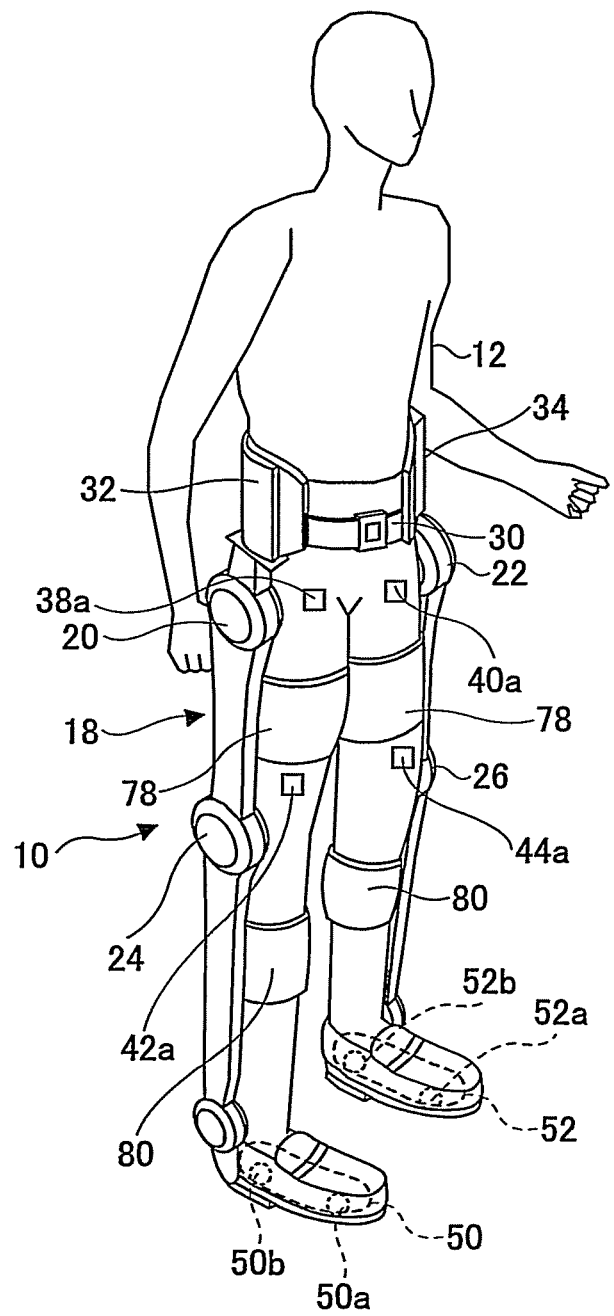
FIG. 1 is a perspective view of a front side of a wearing type action assistance device of an embodiment of the invention which is worn by a person.

DESCRIPTION OF REFERENCE NUMERALS 10 wearing type action assistance device
12 wearing person
18 action-assisting wearing frame
20, 22, 24, 26 drive motor
36 control unit
38a, 38b, 40a, 40b, 42a, 42b, 44a, 44b biosignal detecting sensor
50, 52, 50A, 52A, 50B, 52B, 50C, 52C, 50D, 52D load measuring part 50a, 50b, 52a, 52b reaction sensor
58 first frame
64 first joint
66 second joint
60 second frame
62 third frame
84 shoe
100 lower ground electrode
102 electrode connecting terminal
104 connecting cable
106, 174 ground line
110 lower elastic plate
120 protective rubber plate
130 tiptoe sensing electrode
132, 142 terminal
140 heel sensing electrode
152, 154 core
160 upper elastic plate
170 upper ground electrode
180 protective rubber plate
200 equivalent circuit
300 foot
310 heel
320 tiptoe
330 floor surface
340 moving path
400 control device
410 biosignal processing unit
420 voluntary control unit
430 drive signal generating unit
440 centroid position detecting unit
460 memory
610 lower ground electrode
620 lower elastic layer
630 electrode layer
640 upper elastic layer
650 upper ground electrode
612, 632, 652 flexible wiring board
710 lower electrode sheet
712, 732 electrode wire
720 elastic layer
730 upper electrode sheet

BEST MODE FOR CARRYING OUT THE INVENTION

A description will be given of embodiments of the invention with reference to the accompanying drawings.

Embodiment 1

Figure 2:
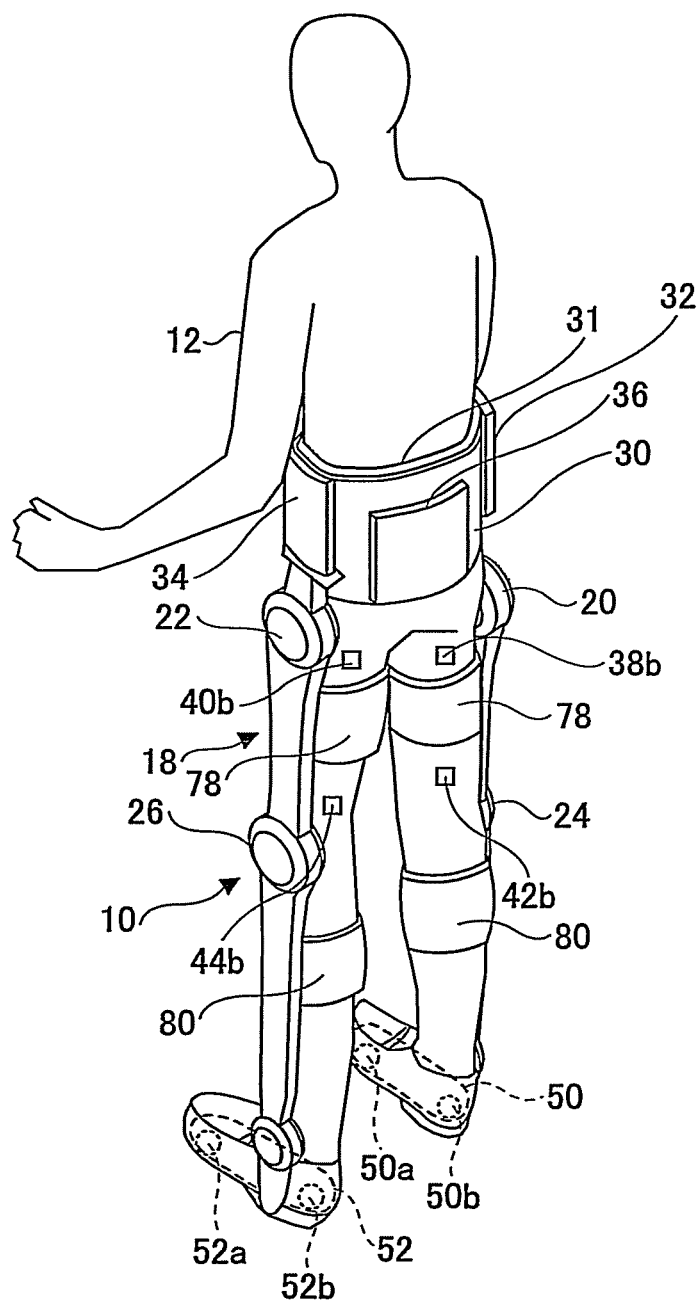
FIG. 2 is a perspective view of a rear side of a wearing type action assistance device of an embodiment of the invention which is worn by a person.

FIG. 1 is a perspective view of a front side of a wearing type action assistance device of an embodiment of the invention which is worn by a wearing person. FIG. 2 is a perspective view of a rear side of the wearing type action assistance device which is worn by the wearing person.

As illustrated in FIGS. 1 and 2, the wearing type action assistance device (which will be referred to as "action assistance device") 10 is to assist a walk action of a person having a difficulty in his own walking ability, such as a disabled person with a troubled leg due to the loss of the muscular strength of a skeletal muscle or a patient who performs rehabilitation of locomotion. The action assistance device 10 detects a biosignal (a muscular line potential) generated when the muscular power is produced in accordance with a signal from the brain, and controls a driving force of the actuator based on the detected signal.

If a wearing person 12 who wears the action assistance device 10 performs a walk action in accordance with his own intention, the driving torque of the actuator according to the biosignal generated according to the walk action is transmitted from the action assistance device 10 to the wearing person as the action assisting force. Hence, the wearing person 12 is able to walk while the total weight is supported by a resultant force of his own muscular power and the driving torque output from the actuator (in this embodiment, an electromotive drive motor is used). Therefore, the wearing person 12 is allowed to walk by a muscular power, namely equivalent to, for example, half the muscular power needed for a normal walk action.

As will be described below, the action assistance device 10 controls the action assisting force (the motor torque) according to a shift of the center of gravity accompanied with a walk action, in order to follow the intention of the wearing person 12. Therefore, the actuator of the action assistance device 10 is controlled to avoid applying a load, namely contrary to the intention of the wearing person 12, and in order not to impede the action of the wearing person 12.

Besides the walk action, the action assistance device 10 may be also used to assist an action of the wearing person 12 when he stands up from a sitting position in which he sits on a chair, or an action of the wearing person 12 when he sits on a chair from a stand-up position. Furthermore, the action assistance device 10 may be also used to assist an action of the wearing person 12 when the wearing person 12 goes up a stairway or goes down a stairway. Especially when the muscular power has weakened, it is difficult to perform the stairway going-up action or the standing-up action from the chair. However, the wearing person 12 who wears the action assistance device 10 is able to receive the driving torque of the actuator according to his own intention, and able to act without caring about deterioration of the muscular power.

Next, the composition of the wearing type action assistance device 10 will be described. As illustrated in FIGS. 1 and 2, the wearing type action assistance device 10 includes an action-assisting wearing frame 18 which is worn by the wearing person 12, and an actuator arranged in the action-assisting wearing frame 18. This actuator includes a right-thigh drive motor 20 disposed at a right-hand side hip joint of the wearing person 12, a left-thigh drive motor 22 disposed at a left-hand side hip joint of the wearing person 12, a right-knee drive motor 24 disposed at a right knee joint of the wearing person 12, and a left-knee drive motor 26 disposed at a left knee joint of the wearing person 12. Each of these drive motors 20, 22, 24, and 26 is made of an electric motor, such as a DC motor or an AC motor, the driving torque of which is controlled by a control signal output from a control device. Each of the drive motors 20, 22, 24, and 26 includes a reduction mechanism (which is built in the actuator) which reduces a rotation speed of the drive motor in accordance with a predetermined reduction ratio. These drive motors are small in size but provide a sufficient driving force. Alternatively, a slim ultrasonic motor may be used as a drive motor, in order to reduce the installation space.

Batteries 32 and 34 are disposed on a belt-like waist fastening member 30 which is attached to the waist of the wearing person 12, and these batteries function as power sources for supplying power to drive the drive motors 20, 22, 24, and 26. The batteries 32 and 34 are rechargeable batteries, and they are arranged on the right and left sides so that they may not interfere with the walk action of the wearing person 12.

A control unit 36 in which a control device 400 (which will be described later) is accommodated is attached to a rear side of the waist fastening member 30 which corresponds to the back side of the wearing person 12.

The action assistance device 10 further includes biosignal detecting sensors 38a and 38b which detect a myoelectricity signal accompanied with a motion of the right thigh of the wearing person 12, biosignal detecting sensors 40a and 40b which detect a myoelectricity signal accompanied with a motion of the left thigh of the wearing person 12, biosignal detecting sensors 42a and 42b which detect a myoelectricity signal accompanied with a motion of the right knee of the wearing person 12, and biosignal detecting sensors 44a and 44b which detect a myoelectricity signal accompanied with a motion of the left knee of the wearing person 12. Each of these biosignal detecting sensors 38a, 38b, 40a, 40b, 42a, 42b, 44a and 44b is a biosignal detecting unit which detects through the skin a myoelectricity signal, such as a muscular line potential signal or a nerve transfer signal. Each biosignal detecting sensor includes electrodes (not illustrated) for detecting a weak electric potential. In this embodiment, each of the biosignal detecting sensors 38a, 38b, 40a, 40b, 42a, 42b, 44a and 44b is stuck on the skin surface of the wearing person 12 with an adhesive seal that covers the periphery of the electrodes of the sensor.

In a human body, acetylcholine as a synaptic transmitter is present to the surface of muscles forming a skeletal muscle according to a command from the brain, and the ion permeability of the muscular fiber film is changed to generate an activation potential. By this activation potential, the muscular fibers are contracted to generate muscular power. Hence, if a muscular line potential signal of the skeletal muscle is detected, estimating muscular power produced in a case of a walk action is possible. Therefore, it is possible to determine an assisting force needed for the walk action, from the virtual torque based on the estimated muscular power.

Accordingly, the action assistance device 10 is arranged so that the driving currents to be supplied to the four drive motors 20, 22, 24, and 26 are determined based on the biosignals detected by the biosignal detecting sensors 38a, 38b, 40a, 40b, 42a, 42b, 44a and 44b, the drive motors 20, 22, 24, and 26 are driven in accordance with the determined driving currents, and the assisting force is given to the wearing person 12 in order to assist the walk action of the wearing person 12.

To smoothly shift a position of the center of gravity of a wearing person 12 during a walk action, it is necessary to detect the position of the center of gravity by detecting the loads on the soles of the wearing person 12. For this purpose, load measuring parts 50 and 52 (which are indicated by the dotted lines in FIGS. 1 2) are arranged on the soles of the right and left feet of the wearing person 12 to measure the loads at a plurality of points on the sole surface.

The load measuring parts 50 and 52 are arranged so that each load measuring part is fitted in intimate contact with the sole surface. The load measuring parts 50 and 52 are arranged so that each load measuring part detects a reaction force which changes according to a shift of the weight of the wearing person accompanied with a walk action.

Figure 3:
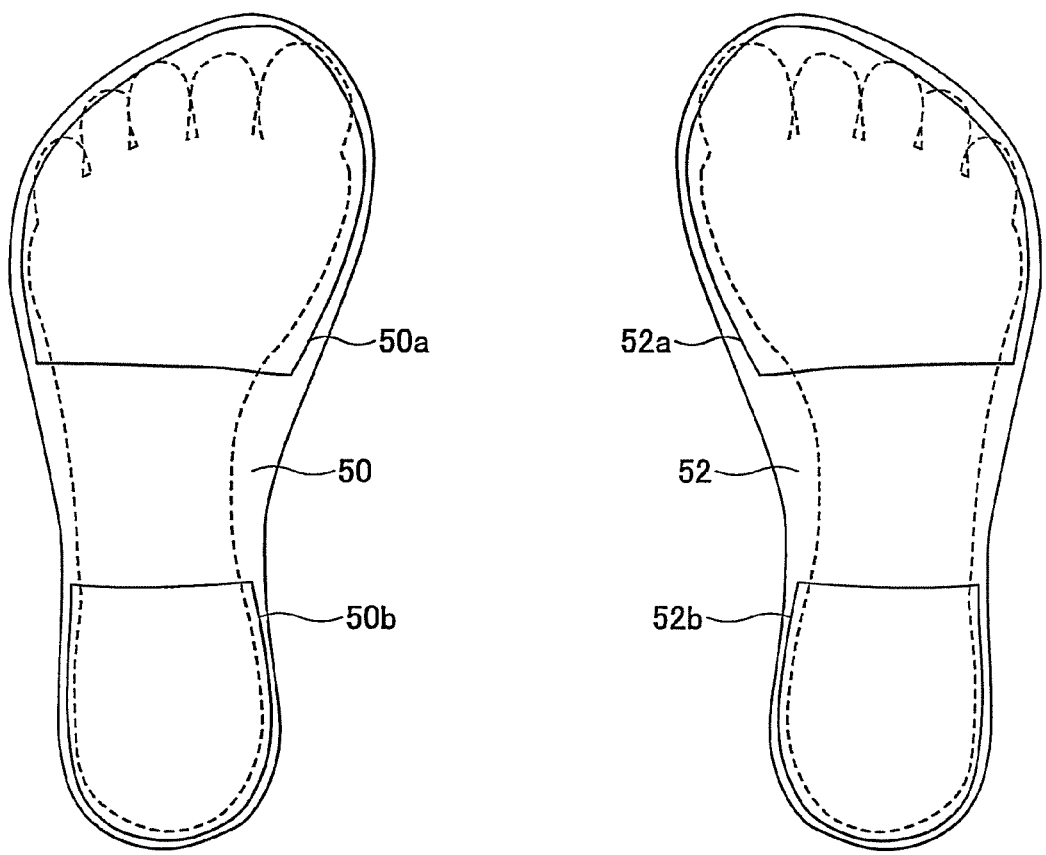
FIG. 3 is a bottom view (backside) of load measuring parts 50 and 52.

FIG. 3 is a bottom view of the load measuring parts 50 and 52. As illustrated in FIG. 3, the load measuring parts 50 and 52 include reaction sensors 50a, 50b, 52a and 52b which are formed to measure two reaction forces to the loads at the tiptoe and the heel on each of the right and left soles of the wearing person 12.

The reaction sensor 50a detects a reaction force Ra to the load on the front side of the right foot (right foot tiptoe), and the reaction sensor 50b detects a reaction force Rb to the load on the rear side of the right foot (right foot heel). The reaction sensor 52a detects a reaction force La to the load on the front side of the left foot (left foot tiptoe), and the reaction sensor 52b detects a reaction force Lb to the load on the rear side of the left foot (left foot heel). Each of these reaction sensors 50a, 50b, 52a and 52b is arranged to detect through a change of a capacitance the load on each of the right foot and the left foot of the wearing person 12 during the walk action. Each reaction sensor can detect a change of the load accompanied with a shift of the weight of the wearing person, and can detect whether the foot of the wearing person 12 is in contact with the ground surface.

Figure 4:
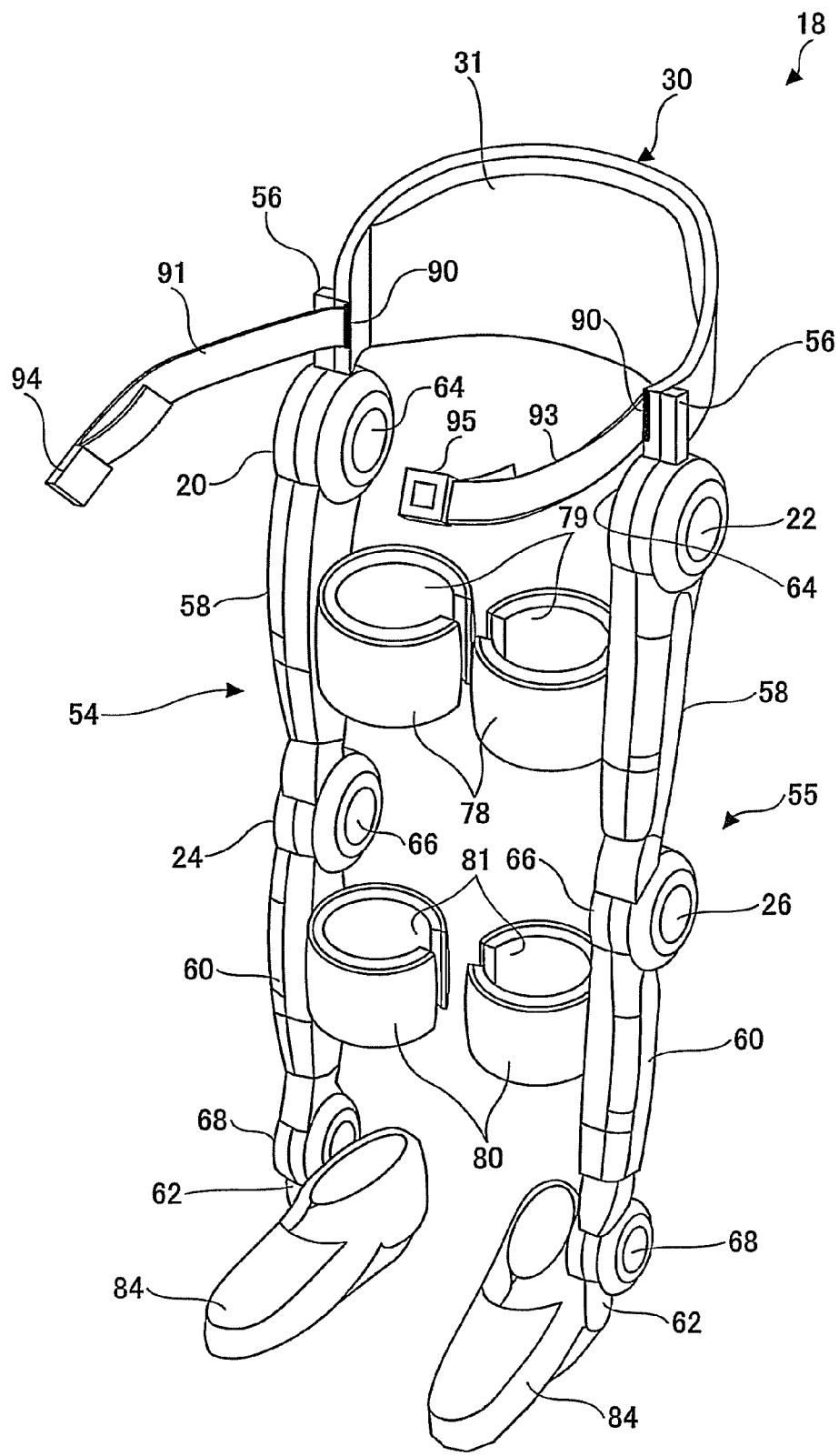
FIG. 4 is a perspective view illustrating a condition of an action-assisting wearing frame 18 before it is worn by a person.

FIG. 4 illustrates a condition of the action-assisting wearing frame 18 before the action-assisting wearing frame 18 is worn by a person. As illustrated in FIG. 4, the action-assisting wearing frame 18 includes a waist fastening member 30 which is attached to the waist of the wearing person 12, a right foot assisting portion 54 which is disposed below the right side part of the waist fastening member 30, and a left foot assisting portion 55 which is disposed below the left side part of the waist fastening member 30. A fitting part 31 is attached to and fitted into contact with the rear side of the waist fastening member 30 to eliminate a gap between the waist fastening member 30 and the rear side of the waist of the wearing person 12.

The right foot assisting portion 54 and the left foot assisting portion 55 are arranged in a symmetrical formation. Each of the assisting portions 54 and 55 includes a bracket 56 which is fixed to the waist fastening member 30, a first frame 58 which is formed to extend downward from the bracket 56 along the outer side of the thigh of the wearing person 12, a second frame 60 which is formed to extend downward from the first frame 58 along the outer side of the knee of the wearing person 12, and a third frame 62 to which the sole of the foot of the wearing person 12 (or the sole of the shoe when the shoes are worn) is attached.

A first joint 64 having a bearing structure is interposed between the lower end of the bracket 56 and the upper end of the first frame 58 and this first joint 64 connects the bracket 56 and the first frame 58 to be rotatable with each other. The first joint 64 is disposed at a height position, namely the same as a height position of the hip joint of the wearing person 12. The bracket 56 is secured to the support side of the first joint 64, and the first frame 58 is secured to the rotation side of the first joint 64. Drive motors 20 and 22 are internally built into the first joint 64, and the appearance of the first joint 64 and the drive motors 20 and 22 is integral.

A second joint 66 having a bearing structure is interposed between the lower end of the first frame 58 and the upper end of the second frame 60, and this second joint 66 connects the second frame 58 and the third frame 62 to be rotatable with each other. The second joint 66 is disposed at a height position, namely the same as a height position of the knee joint of the wearing person 12. The second frame 58 is secured to the support side of the second joint 66, and the third frame 62 is secured to the rotation side of the second joint 66. Drive motors 24 and 26 are internally built in the second joint 66, and the appearance of the second joint 66 and the drive motors 24 and 26 is integral.

A third joint 68 having a bearing structure is interposed between the lower end of the second frame 60 and the upper end of the third frame 62, and this third joint 68 connects the second frame 60 and the third frame 62 to be rotatable with each other. A shoe 84 is secured to the inner side of the third frame 62, and the shoe 84 covers the foot of the wearing person 12.

In this embodiment, the load measuring parts 50 and 52 described above are inserted in the insoles of the shoes 84 respectively. Therefore, when the wearing person 12 wears the shoes 84, the sole sides of the wearing person 12 are held in a condition that the sole sides of the wearing person 12 are fitted in contact with the load measuring parts 50 and 52 inserted in the insoles of the shoes 84. If one of the load measuring parts 50 and 52 fails, the defective part can be easily exchanged with a new part.

Alternatively, the load measuring parts 50 and 52 may be configured into other parts different than the insoles of the shoes 84. For example, the load measuring parts 50 and 52 may be formed into parts which are fitted in contact with the sole sides of socks, tabi-socks, sandals, or slippers.

The first frame 58 is arranged so that the wearing person can perform a walk action using the first joint 64 as a rotational fulcrum to the bracket 56 fixed to the waist fastening member 30. The second frame 60 frame is arranged so that the wearing person can perform a walk action using the second joint 66 as a rotational fulcrum. Namely, the first frame 58 and the second frame 60 are arranged to function in the same manner as the feet of the wearing person 12.

The third joint 68 is arranged so that the third joint 68 is located on the side of the ankle of the wearing person 12. Therefore, the angle of the shoe 84 to the floor surface (or ground surface) changes in accordance with the rotational operation of the third joint 68 during a walk action, similar to that in a case of the ankle of the wearing person 12.

The first joint 64 and the second joint 66 are arranged so that a driving torque from each of the revolving shafts of the drive motors 20, 22, 24, and 26 may be transmitted through the reduction gears to the first frame 58 and the second frame 60.

Each of the drive motors 20, 22, 24, and 26 includes an angle sensor which detects a joint angle. For example, these angle sensors are formed from a rotary encoder which counts the number of pulses proportional to the joint angle of the first joint 64 or the second joint 66, and outputs an electrical signal indicating the number of pulses corresponding to the joint angle as a sensor output.

The angle sensor of the first joint 64 detects a rotation angle between the bracket 56 and the first frame 56 corresponding to a joint angle of the hip joint of the wearing person 12. The angle sensors of the second joint 66 detect a rotation angle between the lower end of the first frame 58 and the second frame 60 corresponding to a joint angle of the knee joint of the wearing person 12.

A belt-like thigh fastening member 78 which is attached to the thigh of the wearing person 12 is attached to an intermediate position of the first frame 58 in the longitudinal direction thereof. A fitting part 79 is attached to and fitted in contact with the inner side of the thigh fastening member 78 to eliminate a gap between the thigh fastening member 78 and the thigh of the wearing person 12.

A belt-like knee fastening member 80 which is attached to the knee of the wearing person 12 is attached to an intermediate position of the second frame 60 in the longitudinal direction thereof. A fitting part 81 is attached to and fitted in contact with the inner side of the knee fastening member 80 to eliminate a gap between the knee fastening member 80 and the knee of the wearing person 12.

Accordingly, a driving torque generated by each of the drive motors 20, 22, 24, and 26 is transmitted through the reduction gear to the first frame 58 and the second frame 60, and further transmitted through the thigh fastening member 78 and the shin fastening member 80 to the foot of the wearing person 12 as the assisting force. Each of the first frame 58 and the second frame 60 is adjusted to have a length equivalent to the length of the foot of the wearing person 12.

Each of the frames 58, 60, and 62 is made of a light-weight, metallic material, such as duralumin, and a resin material having elasticity for covering the periphery of the metallic material, respectively. These frames 58, 60, and 62 are capable of supporting the weight of the assisting wearing frame 18 including the batteries 32 and 34, attached to the waist fastening member 30, and the control unit 36. Namely, the action assistance device 10 is arranged so that the weight of the action-assisting wearing frame 18 and other pars may not act directly on the wearing person 12, and an excessive load may not be applied to the wearing person 12.

The waist fastening member 30 includes two belts 91 and 92 connected via hinges 90 to the waist fastening member 30, a buckle 94 attached to one end of the belt 91, and a fastener 95 attached to one end of the belt 92.

Next, a manufacturing process of the load measuring parts 50 and 52 will be described with reference to FIGS. 5A-5G.

In the following, a description will be given of the load measuring part 50 of the right foot only. Because the load measuring parts 50 and 52 have the same structure, a description of the load measuring part 52 of the left foot will be omitted.

Figure 5A:
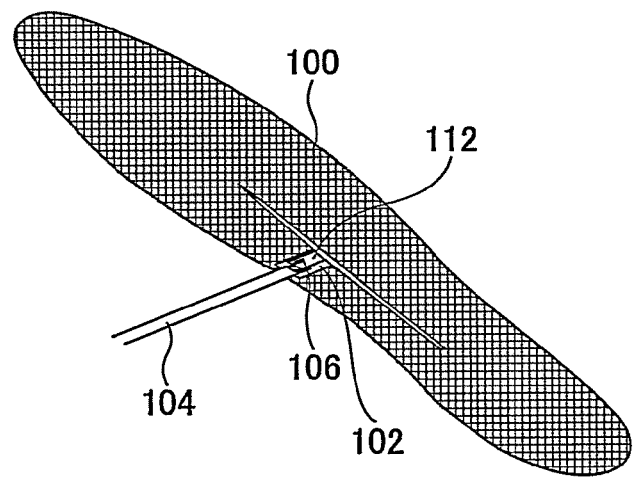
FIG. 5A is a diagram for explaining a manufacturing step 1 of the load measuring part 50 or 52.

As illustrated in FIG. 5A, in a manufacturing step 1, a lower ground electrode 100 is produced. For example, the lower ground electrode 100 is formed by knitted wires of a conductive metal material (for example, a stainless steel material with corrosion resistance) in a mesh formation. The lower ground electrode 100 is arranged to provide flexibility to have the conductive metal material be expanded or contracted according to a motion of the sole side of the foot accompanied with a walk action, without causing disconnection of the loaded portion. An insulating film of a resin material is formed on the top and bottom surfaces of the lower ground electrode 100.

An electrode connecting terminal 102 is formed at the center portion of the lower ground electrode 100. One end of a ground line 106 pulled out from the connecting cable 104 is soldered to the electrode connecting terminal 102. The connecting cable 104 is a two-core shielded cable in which two core wires are covered with braided wires. The other end of the ground line 106 is connected to the braided wires of the connecting cable 104.

Figure 5B:
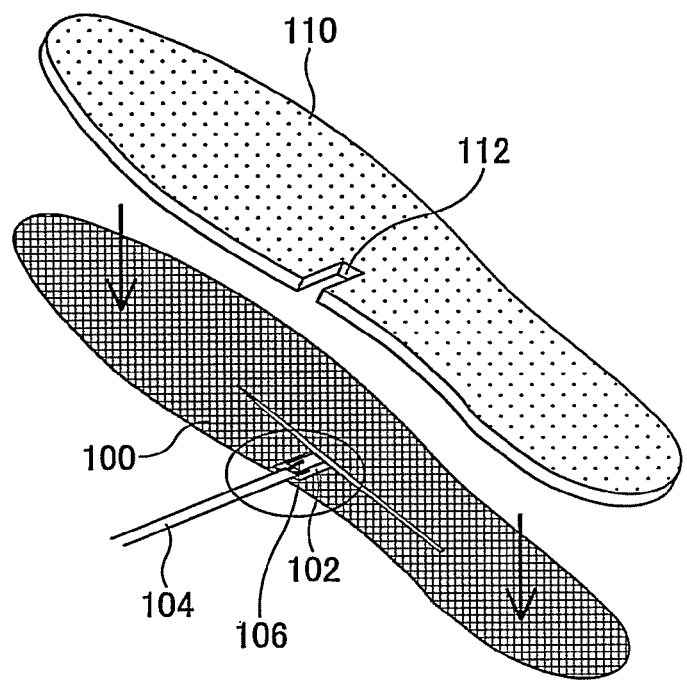
FIG. 5B is a diagram for explaining a manufacturing step 2 of the load measuring part 50 or 52.

As illustrated in FIG. 5B, in a manufacturing step 2, a lower elastic plate 110 is stuck on the top surface of the lower ground electrode 100 with an adhesive agent. The lower elastic plate 110 is a sheet-like insulating material which is formed from a sponge material made of a foam rubber and having elasticity. The lower elastic plate 110 receives a compressive load according to a shift of the weight of the wearing person accompanied with a walk action. In this embodiment, the lower elastic plate 110 is formed to have a thickness of about 3 mm and formed to expand and contract in a range of 1 mm-3 mm according to the magnitude of the applied load. A cut-out opening 112 of a rectangular shape which faces the electrode connecting terminal 102 of the lower ground electrode 100 is formed at the center portion of the lower elastic plate 110.

The rubber hardness of the lower elastic plate 110 is selected depending on the weight of the wearing person 12. For example, a set of lower elastic plates 110 with different hardness levels are beforehand prepared for various weights, including a lower elastic plate of rubber hardness 30 for a weight ranging from 51 kg to 60 kg, a lower elastic plate of rubber hardness 35 for a weight ranging from 61 kg to 70 kg, and a lower elastic plate of rubber hardness 40 for a weight ranging from 71 kg to 80 kg. Therefore, the load measuring parts 50 and 52 are selected depending on the size of the feet of the wearing person 12 and the weight of the wearing person 12.

Because the lower elastic plate 110 is compressed by the reaction force from the floor surface, it is preferred that the sole of the shoe 84 has a sufficiently large hardness so that the reaction force may not be absorbed. However, when the sole of the shoe 84 is made of a rubber material, such as in sports shoes, the hardness of the lower elastic plate 110 may be smaller than that of the sole of the shoe 84, so that the load measurement may be performed stably.

Figure 5C:
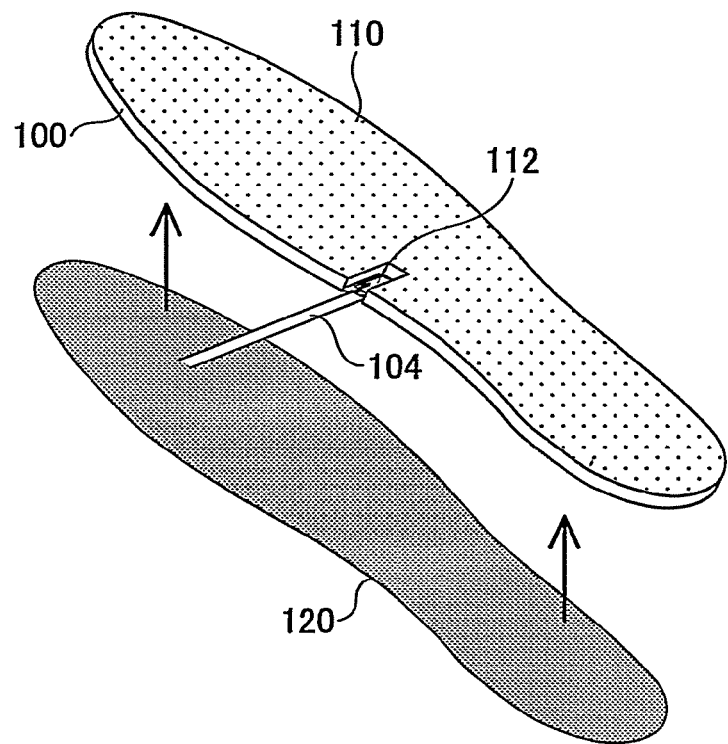
FIG. 5C is a diagram for explaining a manufacturing step 3 of the load measuring part 50 or 52.

As illustrated in FIG. 5C, in a manufacturing step 3, a protective rubber plate 120 having an insulating characteristic is stuck on the bottom surface of the lower ground electrode 100 with an adhesive agent. The protective rubber plate 120 is to protect the lower ground electrode 100 from friction with the inside wall of the shoe 84. The protective rubber plate 120 is stuck to cover the whole bottom surface of the lower ground electrode 100. The protective rubber plate 120 has a thickness smaller than that of the lower elastic plate 110 and is made of a material with hardness greater than that of the lower elastic plate 110, so as not to absorb the reaction force from the floor surface.

Figure 5D:
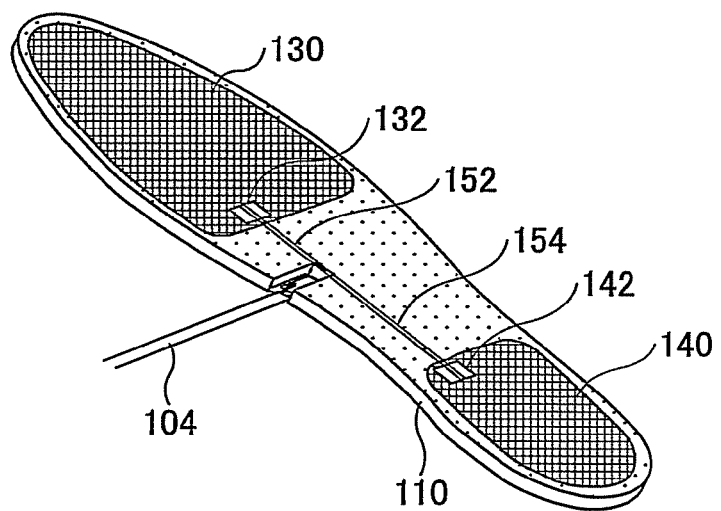
FIG. 5D is a diagram for explaining a manufacturing step 4 of the load measuring part 50 or 52.

As illustrated in FIG. 5D, in a manufacturing step 4, a tiptoe sensing electrode 130 and a heel sensing electrode 140 are stuck on the top surface of the lower elastic plate 110 with an adhesive agent. The tiptoe sensing electrode 130 and the heel sensing electrode 140 constitute the above-described reaction sensors 50a, 50b, 52a and 52b. Similar to the lower ground electrode 100, these electrodes 130 and 140 are formed by knitted wires of a conductive metal material (for example, a stainless steel material with corrosion resistance) in a mesh formation. Hence, the tiptoe sensing electrode 130 and the heel sensing electrode 140 have the respective conductive metal materials being deformed according to a motion of the sole side of the foot accompanied with a walk action so that the loaded parts may not be disconnected. An insulating film of a resin material is formed on the top and bottom surfaces of each of the tiptoe sensing electrode 130 and the heel sensing electrode 140.

One end of each of cores 152 and 154 of the connecting cable 104 for detecting a change of the capacitance according to the applied load is connected to the terminals 132 and 142 of the tiptoe sensing electrode 130 and the heel sensing electrode 140 by soldering. The other end of each of the cores 152 and 154 is connected to a voltage source which supplies a voltage to a capacitor C (refer to FIG. 6) which will be described later.

The tiptoe sensing electrode 130 and the heel sensing electrode 140 are bonded to the locations inside the outer periphery of the lower elastic plate 110, and the outer periphery of the lower elastic plate 110 is exposed to the outside.

Figure 5E:
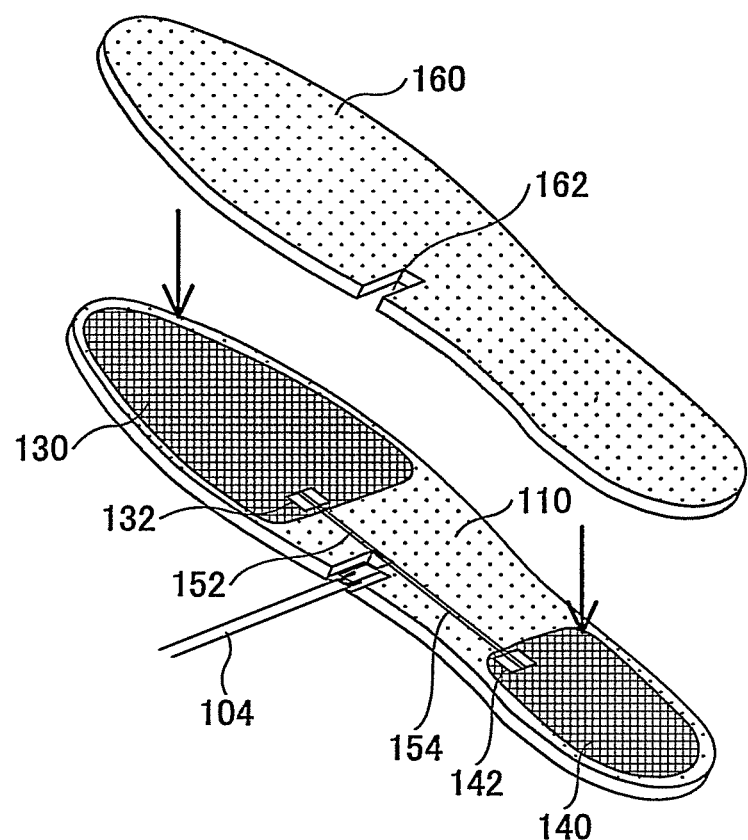
FIG. 5E is a diagram for explaining a manufacturing step 5 of the load measuring part 50 or 52.

As illustrated in FIG. 5E, in a manufacturing step 5, an upper elastic plate 160 is stuck on the top surfaces of the tiptoe sensing electrode 130 and the heel sensing electrode 140, and on the exposed portion of the lower elastic plate 110 with an adhesive agent. Similar to the lower elastic plate 110 described above, the upper elastic plate 160 is made of a sheet-like insulating material which is formed from a sponge material made of a foam rubber and having elasticity. The upper elastic plate 160 receives a compressive load according to a shift of the weight of the wearing person accompanied with a walk action. In this embodiment, the upper elastic plate 160 is formed to have a thickness of about 3 mm and is formed to expand and contract in a range of 1 mm-3 mm according to the magnitude of the applied load. A cut-out opening 162 of a rectangular shape which faces the electrode connecting terminal 102 of the lower ground electrode 100 is formed at the center portion of the upper elastic plate 160.

Similar to the lower elastic plate 110 described above, the rubber hardness of the upper elastic plate 160 is selected depending on the weight of the wearing person 12. For example, a set of upper elastic plates 160 with different hardness levels are beforehand prepared for various weights, including an upper elastic plate of rubber hardness 30 for a weight ranging from 51 kg to 60 kg, an upper elastic plate of rubber hardness 35 for a weight ranging from 61 kg to 70 kg, and an upper elastic plate of rubber hardness 40 for a weight ranging from 71 kg to 80 kg.

Because the upper elastic plate 160 is compressed by the reaction force from the floor surface, it is desirable that the sole of the shoe 84 has a sufficient hardness that prevents the reaction force from being absorbed. However, when the sole of the shoe 84 is made of a rubber material as in a case of sports shoes, the load measurement can be stably performed by making the hardness of the upper elastic plate 160 smaller than that of the sole of the shoe 84.

Figure 5F:
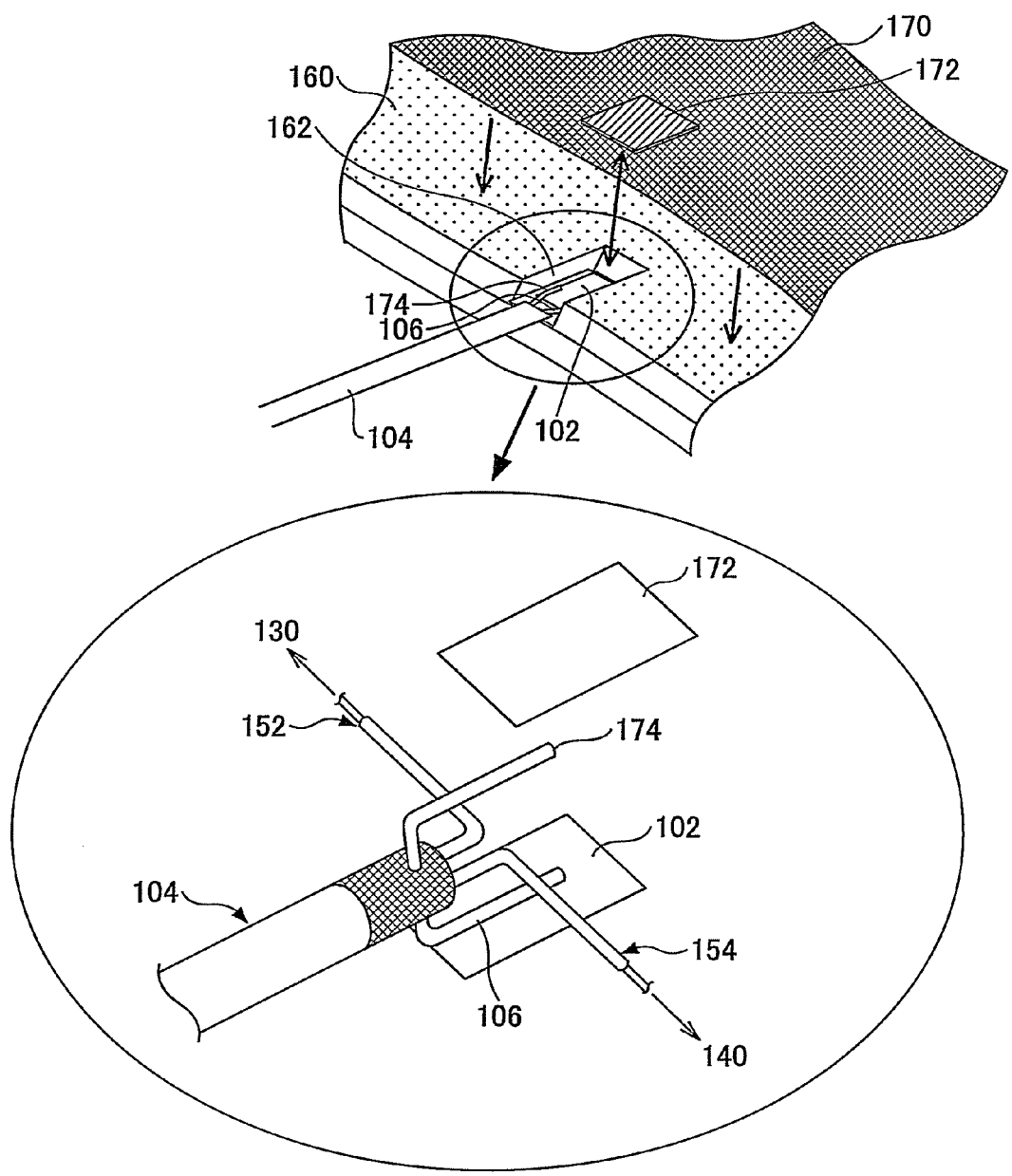
FIG. 5F is a diagram for explaining a manufacturing step 6 of the load measuring part 50 or 52.

As illustrated in FIG. 5F, in a manufacturing step 6, similar to the lower ground electrode 100 described above, one end of a ground line 174 of the connecting cable 104 is soldered to a terminal 172 of the upper ground electrode 170 which is formed by knitted wires of a conductive metal material (for example, a stainless steel material with corrosion resistance) in a mesh formation. The other end of the ground line 174 is connected to the braided wire of the connecting cable 104. The upper ground electrode 170 is bonded to the top surface of the upper elastic plate 160.

The upper ground electrode 170 is formed by the knitted wires of the conductive metal material in the mesh formation. Hence, the upper ground electrode 170 has the respective conductive metal materials being deformed according to a motion of the sole side of the foot accompanied with a walk action so that the loaded parts may not be disconnected. An insulating film of a resin material is formed on the top and bottom surfaces of the upper ground electrode 170.

Figure 5G:
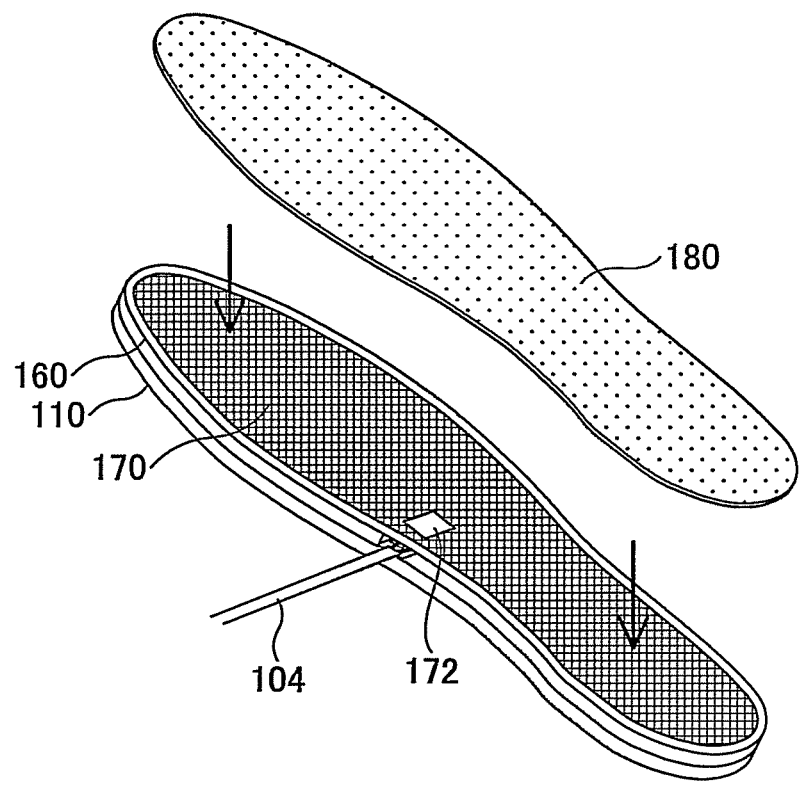
FIG. 5G is a diagram for explaining a manufacturing step 7 of the load measuring part 50 or 52.

As illustrated in FIG. 5G, in a manufacturing step 7, a protective rubber plate 180 having an insulating characteristic is stuck on the top surface of the upper ground electrode 170 with an adhesive agent. Similar to the protective rubber plate 120 described above, the protective rubber plate 180 is to protect the upper ground electrode 170 from friction with the sole side of the foot of the wearing person 12. The protective rubber plate 180 is stuck to cover the whole top surface of the upper ground electrode 170. The protective rubber plate 180 has a thickness smaller than that of the lower elastic plate 110 or the upper elastic plate 160, and is made of a material with hardness greater than that of the lower elastic plate 110 or the upper elastic plate 160 so as not to absorb the reaction force from the floor surface.

As described in the foregoing, the load measuring parts 50 and 52 of this embodiment is arranged such that the protective rubber plate 120, the lower ground electrode 100, the lower elastic plate 110, the tiptoe sensing electrode 130 and the heel sensing electrode 140, the upper elastic plate 160, the upper ground electrode 170, and the protective rubber plate 180 are laminated from the bottom in this order and bonded together.

In this embodiment, the tiptoe sensing electrode 130 and the heel sensing electrode 140 are interposed between the lower ground electrode 100 and the upper ground electrode 170, and the tiptoe sensing electrode 130 and the heel sensing electrode 140 are shielded from electromagnetic waves by the lower ground electrode 100 and the upper ground electrode 170. For this reason, the signals detected from the tiptoe sensing electrode 130 and the heel sensing electrode 140 are not influenced by external noises, and it is possible to increase the accuracy of the detection using the tiptoe sensing electrode 130 and the heel sensing electrode 140.

Figure 6:
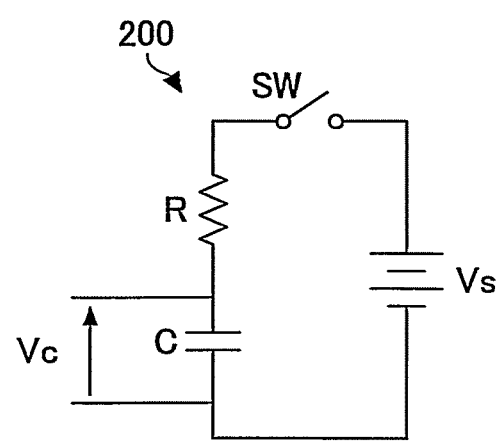
FIG. 6 is a circuit diagram illustrating an equivalent circuit of the load measuring part 50 or 52.

FIG. 6 illustrates an equivalent circuit of the load measuring part 50 or 52. As illustrated in FIG. 6, the equivalent circuit 200 is arranged to detect a capacitance according to each of a vertical-direction distance between the tiptoe sensing electrode 130 and the lower ground electrode 100, a vertical-direction distance between the tiptoe sensing electrode 130 and the upper ground electrode 170, a vertical-direction distance between the heel sensing electrode 140 and the lower ground electrode 100, and a vertical-direction distance between the heel sensing electrode 140 and the upper ground electrode 170.

In the equivalent circuit 200, if the switch SW is turned from an OFF state to an ON state, storing electric charge in the capacitor C is started. An electric potential difference Vc between the ends of the capacitor C will be increased from zero volt in a charging time proportional to a distance between the electrodes of the capacitor C. Therefore, according to the equivalent circuit 200, the charging time is varied in accordance with the capacitance of the capacitor C, and a capacitance can be measured by measuring a time the electric potential difference Vc of capacitor C reaches a predetermined value Vx after an end of discharging.

Figure 7:
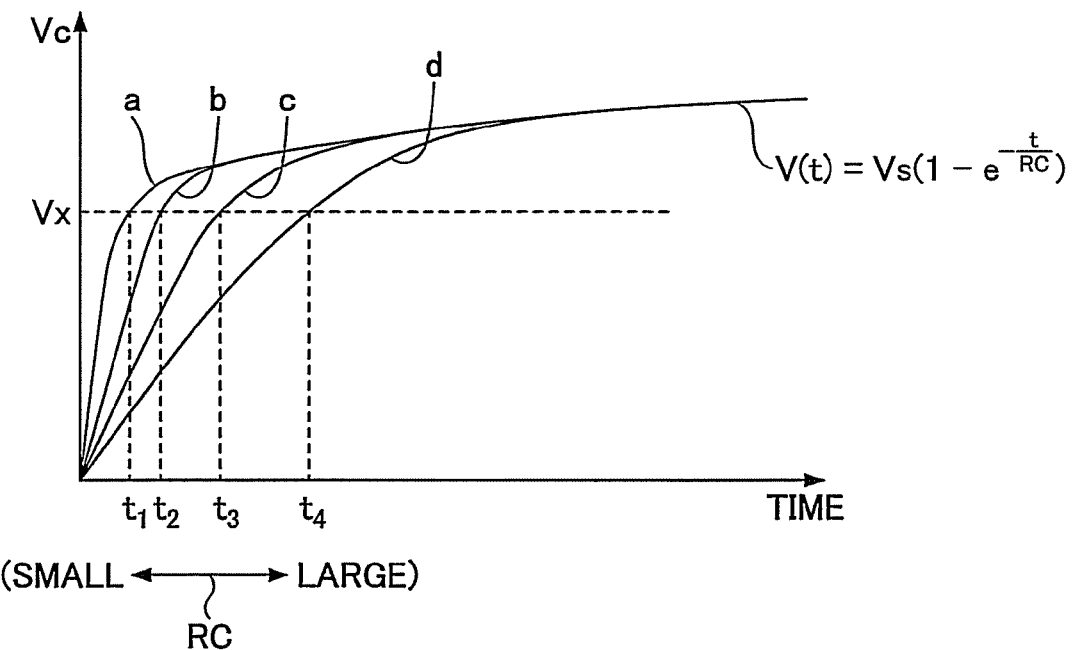
FIG. 7 is a diagram for explaining a change of a voltage of a capacitor C (reaction sensor).

FIG. 7 is a diagram for explaining a change of a voltage of a capacitor C (reaction sensor). As illustrated in FIG. 7, a charge rate of a voltage of the capacitor C is changed in accordance with the function (RC) which is expressed in the following formula (1).

$$V(t)=Vs(1-e^{-t/RC}) \quad (1)$$

For example, as indicated by the graphs a, b, c, and d in FIG. 7, the time required for the electric potential difference Vc of the capacitor C to reach the predetermined value Vx is changed in accordance with the capacitance of the capacitor C and a resistor R (constant resistance), like t1, t2, t3, and t4. Namely, the resistance of the resistor R is constant, and the capacitance of the capacitor C is decreased as the distance between the electrodes of the capacitor C is decreased, while the capacitance of the capacitor C is increased as the distance between the electrodes of the capacitor C is increased. Hence, the distance between the electrodes of the capacitor C can be determined based on the charging time of the capacitor C.

In this embodiment, the tiptoe sensing electrode 130 (or the heel sensing electrode 140) and the lower ground electrode 100 constitutes a capacitor C, the tiptoe sensing electrode 130 (or the heel sensing electrode 140) and the upper ground electrode 170 constitutes a capacitor C, and a capacitance of each capacitor C is changed in accordance with the vertical-direction distance between the tiptoe sensing electrode 130 (or the heel sensing electrode 140) and the lower ground electrode 100, and the vertical-direction distance between the tiptoe sensing electrode 130 (or the heel sensing electrode 140) and the upper ground electrode 170. Therefore, the load measuring parts 50 and 52 detect these capacitance values so that the ratio of the weights (loads) of the wearing person on the sole sides of the feet of the wearing person can be determined.

FIGS. 8A-8D are diagrams for explaining operation of the load measuring parts 50 and 52 associated with a motion of the sole of the foot of the wearing person 12. The right and left feet of the wearing person 12 are moved symmetrically in this case, and the motions of the right and left feet are alternately performed in succession. A description will be given of operation of the load measuring part 50 or 52 associated with a motion of one foot when the wearing person 12 moves forward.

Figure 8A:
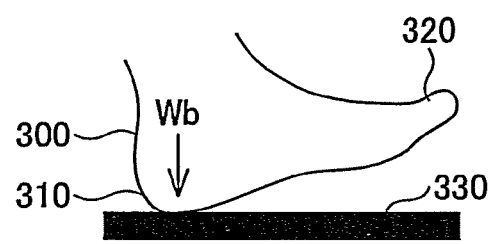
FIG. 8A is a diagram for explaining operation of the load measuring part 50 or 52 when a heel of a wearing person 12 contacts a floor surface.
Figure 8A:
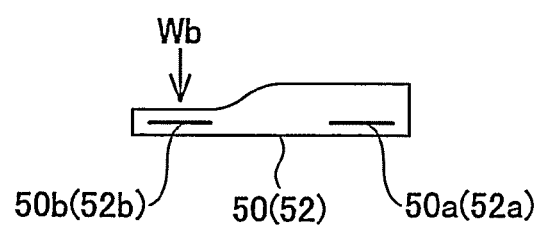

As illustrated in FIG. 8A, when the heel 310 of the foot 300 of the wearing person 12 has contacted the floor surface 330 (at this time, the tiptoe of the other foot is in contact with the floor surface), a load Wb acts on the reaction sensor 50b (52b) of the load measuring part 50 (52). Namely, the parts of the lower elastic plate 110 and the upper elastic plate 160, facing the heel sensing electrode 140, are compressed by the load Wb. Thereby, the vertical-direction distance between the lower ground electrode 100 (or the upper ground electrode 170) and the heel sensing electrode 140 is decreased, and the capacitance of the capacitor is decreased. This operating state is equivalent to the detecting state indicated by the graph c in FIG. 7.

Figure 8B:
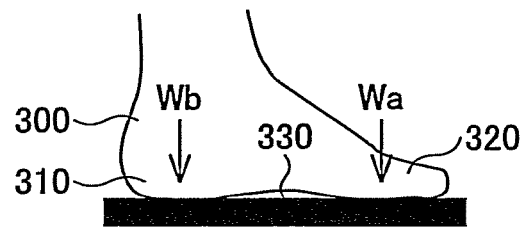
FIG. 8B is a diagram for explaining operation of the load measuring part 50 or 52 when the sole surface of the wearing person 12 contacts the floor surface.
Figure 8B:
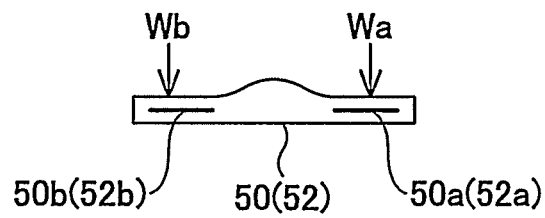

As illustrated in FIG. 8B, when the motion of the foot 300 of the wearing person 12 progresses and the heel 310 and the tiptoe 320 have contacted the floor surface 330 (at this time, the sole surface of the other foot is separated from the floor surface), a load Wb acts on the reaction sensor 50b (52b) of the load measuring part 50 (52) and a load Wa acts on the reaction sensor 50a (52a) of the load measuring part 50 (52). Namely, the parts of the lower elastic plate 110 and the upper elastic plate 160, facing the tiptoe sensing electrode 130 and the heel sensing electrode 140, are compressed by the loads Wa and Wb. Thereby, the vertical-direction distance between the lower ground electrode 100 (or the upper ground electrode 170) and the tiptoe sensing electrode 130 and the vertical-direction distance between the lower ground electrode 100 (or the upper ground electrode 170) and the heel sensing electrode 140 are decreased, and the capacitances at the tiptoe and the heel are decreased. This operating state is equivalent to the detecting state indicated by the graph a in FIG. 7.

Figure 8C:
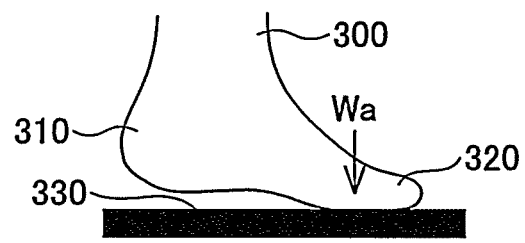
FIG. 8C is a diagram for explaining operation of the load measuring part 50 or 52 when only a tiptoe of the wearing person 12 contacts the floor surface.
Figure 8C:
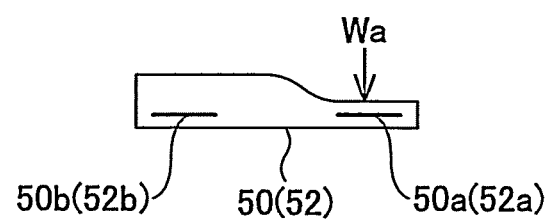

As illustrated in FIG. 8C, when the motion of the foot 300 of the wearing person 12 progresses further and the heel 310 has separated from the floor surface 330 and the tiptoe 320 has contacted the floor surface 330 (at this time, the heel of the other foot is in contact with the floor surface), only a load Wa acts on the reaction sensor 50a (52a) of the load measuring part 50 (52). Namely, the parts of the lower elastic plate 110 and the upper elastic plate 160, facing the tiptoe sensing electrode 130, are compressed by the load Wa. Thereby, the vertical-direction distance between the lower ground electrode 100 (or the upper ground electrode 170) and the tiptoe sensing electrode 130 is decreased, and the capacitance at the tiptoe is decreased. This operating state is equivalent to the detecting state indicated by the graph b in FIG. 7.

Figure 8D:
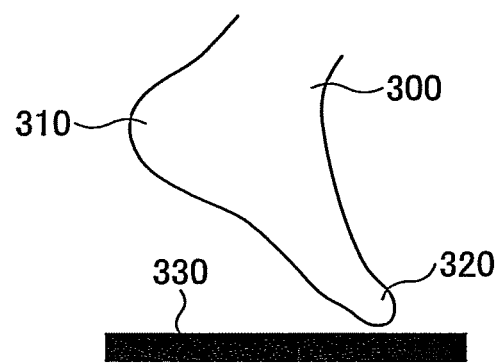
FIG. 8D is a diagram for explaining operation of the load measuring part 50 or 52 when the foot of the wearing person 12 is separated from the floor surface.
Figure 8D:
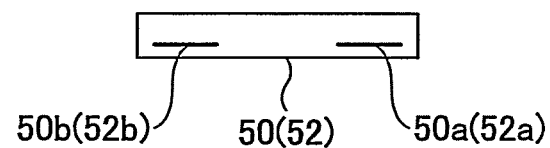

As illustrated in FIG. 8D, when the motion of the wearing person 12 foot 300 progresses further and the tiptoe 320 has also separated from the floor surface 330 (at this time, the heel and the tiptoe of the other foot are in contact with the floor surface), no load acts on the reaction sensor 50a (52a) of the load measuring part 50 (52). Namely, the lower elastic plate 110 and the upper elastic plate 160 are not compressed, and the load measuring part 50 (52) is returned to the original state in which no load acts thereon. The vertical-direction distance between the lower ground electrode 100 (or the upper ground electrode 170) and the tiptoe sensing electrode 130 and the vertical-direction distance between the lower ground electrode 100 (or the upper ground electrode 170) and the heel sensing electrode 140 are increased, and the capacitances at the tiptoe and the heel are increased. This operating state is equivalent to the detecting state indicated by the graph d in FIG. 7.

In this manner, it is possible to determine the operating state of the wearing person 12 during the walk action (a change of the load on the tiptoe or the heel) based on the values of the detection signals of the capacitance output from the tiptoe sensing electrode 130 and the heel sensing electrode 140 (which indicate the time the predetermined reference voltage is reached).

Figure 9:
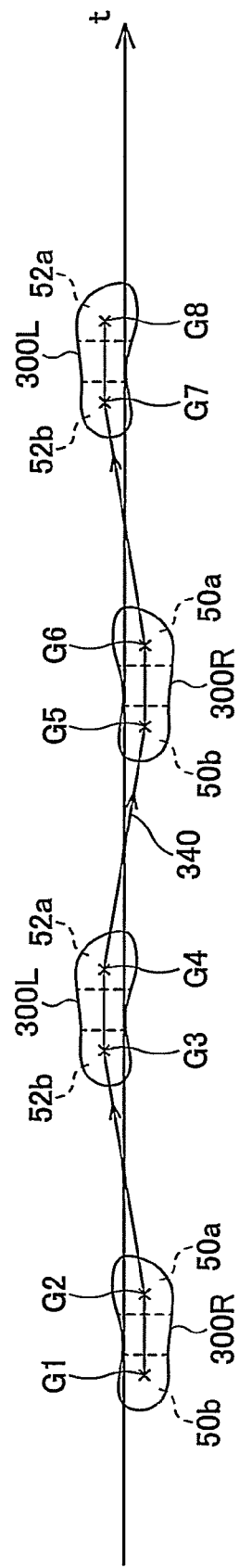
FIG. 9 is a top view of the locus of shifts of a center of gravity of a wearing person accompanied with a walk action of the wearing person.

FIG. 9 is a top view of the locus of shifts of the center of gravity of a wearing person accompanied with a walk action of the wearing person. As illustrated in FIG. 9, when the wearing person 12 walks while alternately moving the right foot 300R and the left foot 300L forward, the center of gravity of the wearing person 12 is moved as indicated by the points G1 to G8 in FIG. 9. For example, if the wearing person 12 moves the right foot 300R forward, the weight acts on the heel (G1) of the right foot 300R, and the center of gravity is moved to the front side of the wearing person 12. Subsequently, if the left foot 300L of the wearing person 12 is separated from the floor surface and the body is leaned in the forward direction, the weight acts on the heel (G1) and the tiptoe (G2) of the right foot 300R, and the center of gravity is moved to the front side of the wearing person 12.

Subsequently, if the left foot 300L of the wearing person 12 is moved forward of the right foot 300R, the heel (G1) of the right foot 300R is separated from the floor surface, the weight acts on the tiptoe (G2) of the right foot 300R and the heel (G3) of the left foot 300L, and the center of gravity is moved to the front side of the wearing person 12.

In this manner, as the wearing person 12 alternately moves the right foot 300R and the left foot 300L forward, the point where the weight of the wearing person 12 acts is moved as indicated by the points G1 to G8 in FIG. 9. Therefore, the line linking the points G1 to G8 where the weight of the wearing person 12 acts forms a moving path 340 of the center of gravity. The center of gravity is moved along the line linking the landing points (where the wearing person receives the reaction force from the floor surface) of the right foot 300R and the left foot 300L, as illustrated in FIG. 9.

In this embodiment, a position of the center of gravity of the wearing person 12 can be determined based on the detection signals output from the tiptoe sensing electrode 130 and the heel sensing electrode 140, which indicate the capacitance of the capacitor. Namely, changes of the respective loads are computed based on the detection signals output from the reaction sensors 50a, 50b, 52a and 52b of the load measuring parts 50 and 52, under the control of the control device which will be described later. Furthermore, a position of the center of gravity of the wearing person 12 in the sole surface is computed based on the ratio of the detected loads, and the position of the center of gravity accompanied with the walk action is determined.

In the action assistance device 10, the timing of generating the driving torque for each of the drive motors 20, 22, 24, and 26 is controlled based on the detection data of such centroid position. Namely, the above control makes it possible to match the timing of the action assistance device 10 to drive the right-hand side drive motors 20 and 24 with the timing of the wearing person 12 to move the right foot 300R forward. Similarly, the above control makes it possible to match the timing of the action assistance device 10 to drive the left-hand side drive motors 22 and 26 with the timing of the wearing person 12 to move the left foot 300L forward.

Figure 10:
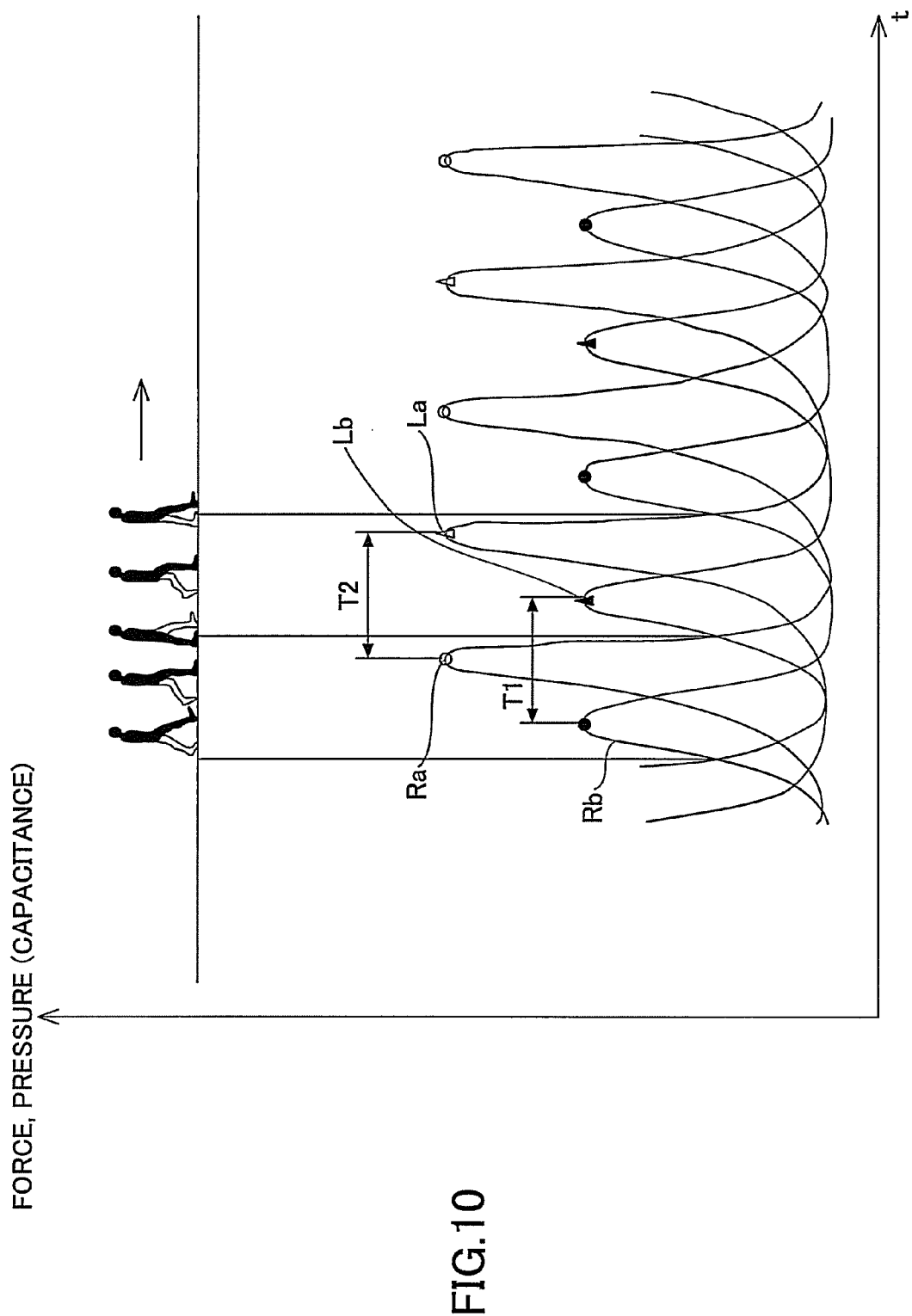
FIG. 10 is a diagram for explaining transitional changes of detection signals output from reaction sensors $50a$, $50b$, $52a$ and $52b$.

FIG. 10 is a diagram for explaining transitional changes of detection signals output from the reaction sensors 50a, 50b, 52a and 52b. As illustrated in FIG. 10, the detection signals Ra, Rb, La and Lb of the reaction sensors 50a, 50b, 52a and 52b are periodically increased and decreased according to the walk action of the wearing person 12.

For example, the detection signal Rb of the reaction sensor 50b of the right foot 300R reaches the peak in the amplitude when the heel 310 of the right foot 300R has contacted the floor surface (refer to FIG. 8A), and the detection signal Ra of the reaction sensor 50a of the right foot 300R reaches the peak in the amplitude when only the tiptoe 320 of the right foot 300R has contacted the floor surface (refer to FIG. 8C).

Furthermore, with a phase difference T1 from the peak time of the reaction sensor 50b of the right foot 300R, the detection signal Lb of the reaction sensor 52b of the left foot 300L reaches the peak in the amplitude when the heel 310 of the left foot 300R has contacted the floor surface (refer to FIG. 8A). With a phase difference T2 from the peak time of the reaction sensor 50a of the right foot 300R, the detection signal La of the reaction sensor 52a of the left foot 300L reaches the peak in the amplitude when only the tiptoe 320 of the right foot 300R has contacted the floor surface (refer to FIG. 8C).

In this manner, when the wearing person 12 walks in a fixed rhythm, the detection signals Ra, Rb, La and Lb output from the reaction sensors 50a, 50b, 52a and 52b are periodically increased and decreased with a predetermined phase difference. Therefore, it is possible to estimate a shift of the center of gravity of the wearing person by comparing the detection signals Ra, Rb, La and Lb of the reaction sensors 50a, 50b, 52a and 52b with respect to each other with progress of time.

Figure 11:
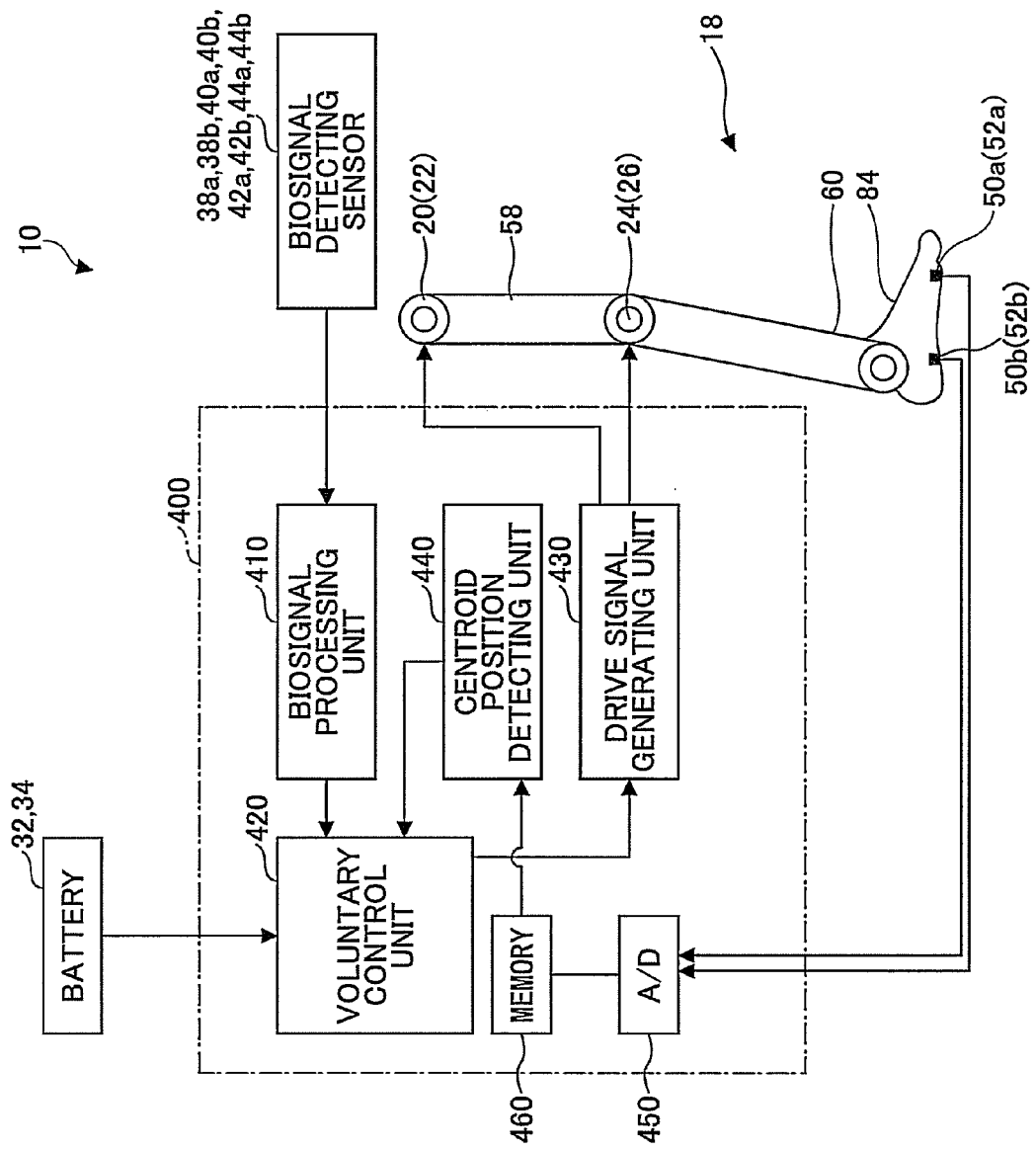
FIG. 11 is a block diagram illustrating the composition of a wearing type action assistance device in which an action-assisting wearing frame 18 and a control device 400 are associated with each other.

FIG. 11 illustrates the composition of a wearing type action assistance device in which an action-assisting wearing frame 18 and a control device 400 are associated with each other. As illustrated in FIG. 11, the control device 400 which is disposed in the control unit 36 is a microcomputer which performs computations. The control device 400 includes a memory 460 in which a plurality of control programs are stored beforehand. The control device 400 performs respective control processes (which will be described later) by loading the control programs from the memory 460.

In this embodiment, the control device 400 includes: a biosignal processing unit 410 which acquires a command signal from each of the biosignals detected by the biosignal detecting sensors 38a, 38b, 40a, 40b, 42a, 42b, 44a and 44b; a voluntary control unit 420 which controls driving of each of the motors 20, 22, 24, and 26 based on a nerve transfer signal and a muscular line potential signal; a drive signal generating unit 430 which generates a drive signal according to a control signal output from the voluntary control unit 420 and outputs the drive signal to each motor; and a centroid position detecting unit 440 which detects a position of the center of gravity of the wearing person 12 based on the detection signals Ra, Rb, La and Lb of the reaction sensors 50a, 50b, 52a and 52b.

In this embodiment, an exemplary motor control method which controls the current to be supplied to each motor as a drive signal will be described.

The biosignal processing unit 410 generates a nerve transfer signal and a muscular line potential signal from a myoelectricity potential produced when the right or left foot is operated according to the intention of the wearing person 12. The voluntary control unit 420 outputs a control signal to the drive signal generating unit 430 based on a command signal from the biosignal processing unit 410. The drive signal generating unit 430 generates a driving current according to the control signal from the voluntary control unit 420 and outputs the driving current to each of the motors 20, 22, 24, and 26.

During a walk action by the wearing person 12, the reaction sensors 50a, 50b, 52a and 52b output the detection signals Ra, Rb, La and Lb according to the walk action (which signals indicate the capacitance of the capacitor). These detection signals Ra, Rb, La and Lb are converted into digital signals by an A/D converter 450, and the digital signals are stored in the memory 460, Furthermore, the digital signals from the memory 460 are supplied to the centroid position detecting unit 440.

Next, a reaction sensor calibration process which is performed by the control device 400 will be described with reference to FIG. 12. The control process illustrated in FIG. 12 is performed after the wearing person 12 wears the action-assisting wearing frame 18 and has the shoes 84 on the feet of the wearing person 12.

Figure 12:
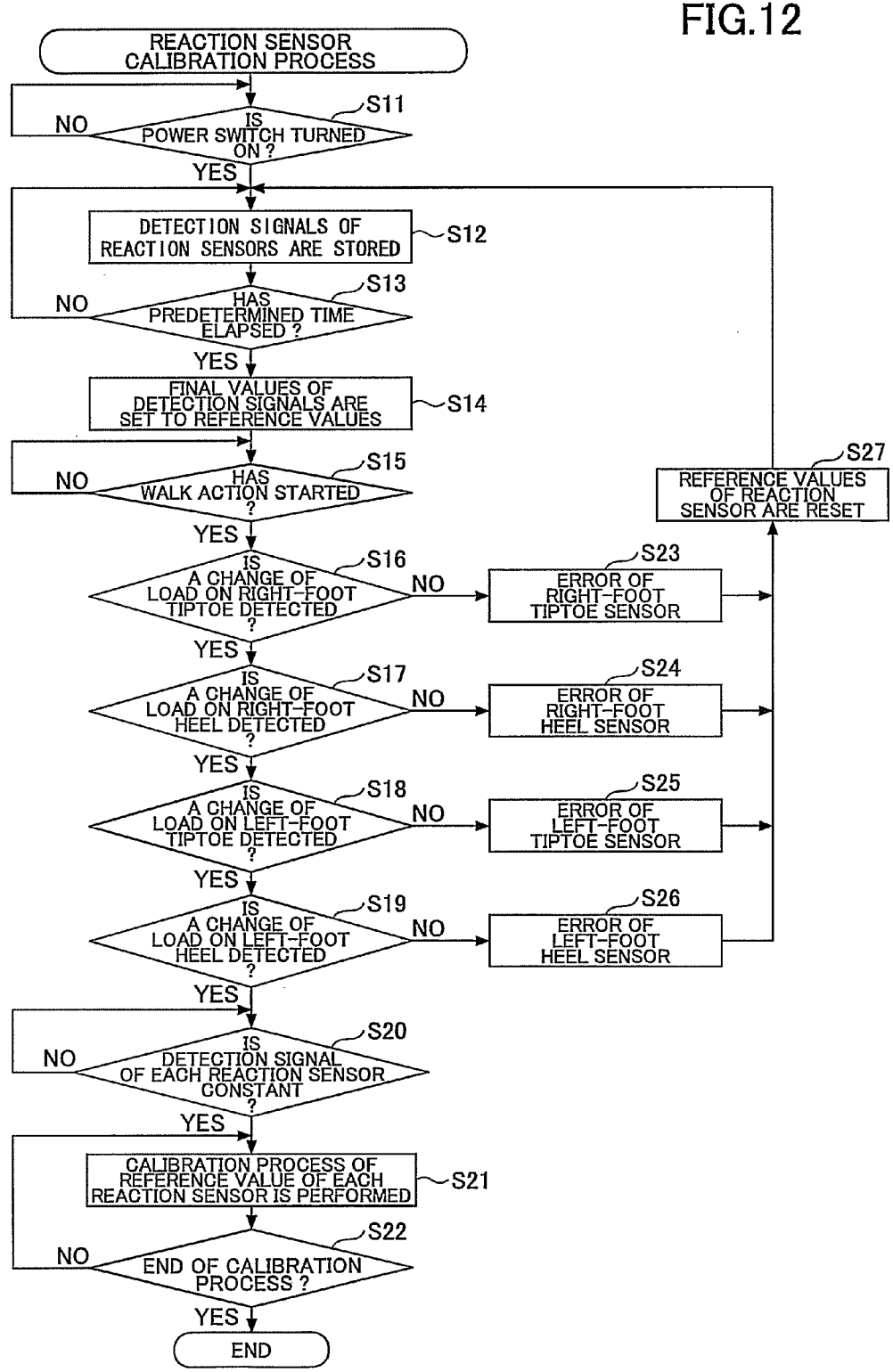
FIG. 12 is a flowchart for explaining a reaction sensor calibration process which is performed by the control device 400.

As illustrated in FIG. 12, if it is detected in S11 that the power switch of the action assistance device 10 is turned ON by the wearing person 12 who wears the action-assisting wearing frame 18, the control by the control device 400 progresses to S12. In S12, the control device 400 reads out the detection signals Ra, Rb, La and Lb of the reaction sensors 50a, 50b, 52a and 52b (which indicate the capacitance of the capacitor) and stores the capacitances indicated by the detection signals Ra, Rb, La and Lb in the memory 460.

Subsequently, it is detected in S13 whether a predetermined time (for example, 5 to 10 seconds) has elapsed. If the detection signals Ra, Rb, La and Lb of the reaction sensors 50a, 50b, 52a and 52b are changed before the predetermined time has elapsed, the detection data previously stored in the memory 460 are updated by a latest version of the detection data.

When it is detected in S13 that the predetermined time has elapsed, the control progress to S14. In S14, the final values of the detection signals Ra, Rb, La and Lb of the reaction sensors 50a, 50b, 52a and 52b are set to reference values (initial values).

Subsequently, it is detected in S15 whether the wearing person 12 has started a walk action. For example, when the biosignals are output from the biosignal detecting sensors 38a, 38b, 40a, 40b, 42a, 42b, 44a and 44b accompanied with a standup action of the wearing person 12 started from the sitting position in which the wearing person 12 has been sitting on a chair, it is determined that the walk action is started. As for the detection of the centroid position accompanied with a standup action of the wearing person 12 from the sitting position, by using output data of sensors other than the reaction sensors 50a, 50b, 52a and 52b (for example, capacitance-type reaction sensors may be disposed in the hip part of the wearing person 12) additionally, it can be detected that the standup action is started.

Subsequently, it is detected in S16 whether a change of the load on the right-foot tiptoe is detected by the reaction sensor 50a. When it is detected in S16 that the detection signal Ra of the reaction sensor 50a is changed, the control progresses to S17. It is detected in S17 whether a change of the load on the right-foot heel is detected by the reaction sensor 50b.

When it is detected in S17 that the detection signal Rb of the reaction sensor 50b is changed, the control progresses to S18. It is detected in S18 whether a change of the load on the right-foot tiptoe is detected by the reaction sensor 52a. When it is detected in S18 that the detection signal La of the reaction sensor 52a is changed, the control progresses to S19. It is detected in S19 whether a change of the load on the left-foot heel is detected by the reaction sensor 52b.

When it is detected in S19 that a change of the load on the left-foot heel is detected by the reaction sensor 52b, the control progresses to S20. In S20, the detection signals Ra, Rb, La and Lb of the reaction sensors 50a, 50b, 52a and 52b in the standup position in which the wearing person 12 stands up and does not move are read.

Subsequently, in S21, the control device 400 performs a calibration process of the reference values (initial values) of the reaction sensors 50a, 50b, 52a and 52b. Namely, the detection signals Ra, Rb, La and Lb of the reaction sensors 50a, 50b, 52a and 52b which are output when the walking position is shifted to the standup position are read, and the initially stored signals are updated by the currently read signals as the newest reference values. Hence, the reference values detected immediately after the wearing person 12 wears the action-assisting wearing frame 18 are updated by the newest reference values to which the detection data are changed by the walk action of the wearing person 12. Thereby, the reference values may be updated by the calibration process even when the fittings between the feet of the wearing person 12 and the shoes 84 are modified or the action of the wearing person 12 fluctuates on a daily basis according to his physical condition.

It is detected in S22 whether the calibration process is completed for the reference values of the respective reaction sensors. When it is detected in S22 that the calibration process is completed, this control process is terminated.

When it is detected in S16 that the detection signal Ra of the reaction sensor 50a is not changed, the control progresses to S23. It is determined in 323 that an error of the reaction sensor 50a takes place, and the control progresses to 327. In 327, the reference value of the reaction sensor 50a is reset.

When it is detected in S17 that the detection signal Rb of the reaction sensor 50b is not changed, the control progresses to S24. It is determined in S24 that an error of the reaction sensor 50b takes place, and the control progresses to S27. In S27, the reference value of the reaction sensor 50b is reset.

When it is detected in S18 that the detection signal La of the reaction sensor 52a is not changed, the control progresses to S25. It is determined in 325 that an error of the reaction sensor 52a takes place, and the control progresses to S27. In S27, the reference value of the reaction sensor 52a is reset.

When it is detected in S19 that the detection signal Lb of the reaction sensor 52b is not changed, the control progresses to 526. It is determined in 326 that an error of the reaction sensor 52b takes place, and the control progresses to S27. In S27, the reference value of the reaction sensor 52b is reset.

After the step S27 is performed, the control is returned to the step S12 and the subsequent steps are performed repeatedly. If the load measuring part 50 or 52 is to be exchanged by a new part, this control process is stopped. The repairing work of the reaction sensor can be performed in a short time.

After the above-described calibration process is completed, the wearing person 12 starts a walk action.

Next, a centroid position detection process 1 which is performed by the control device 400 accompanied with a walk action will be described with reference to FIG. 13.

Figure 13:
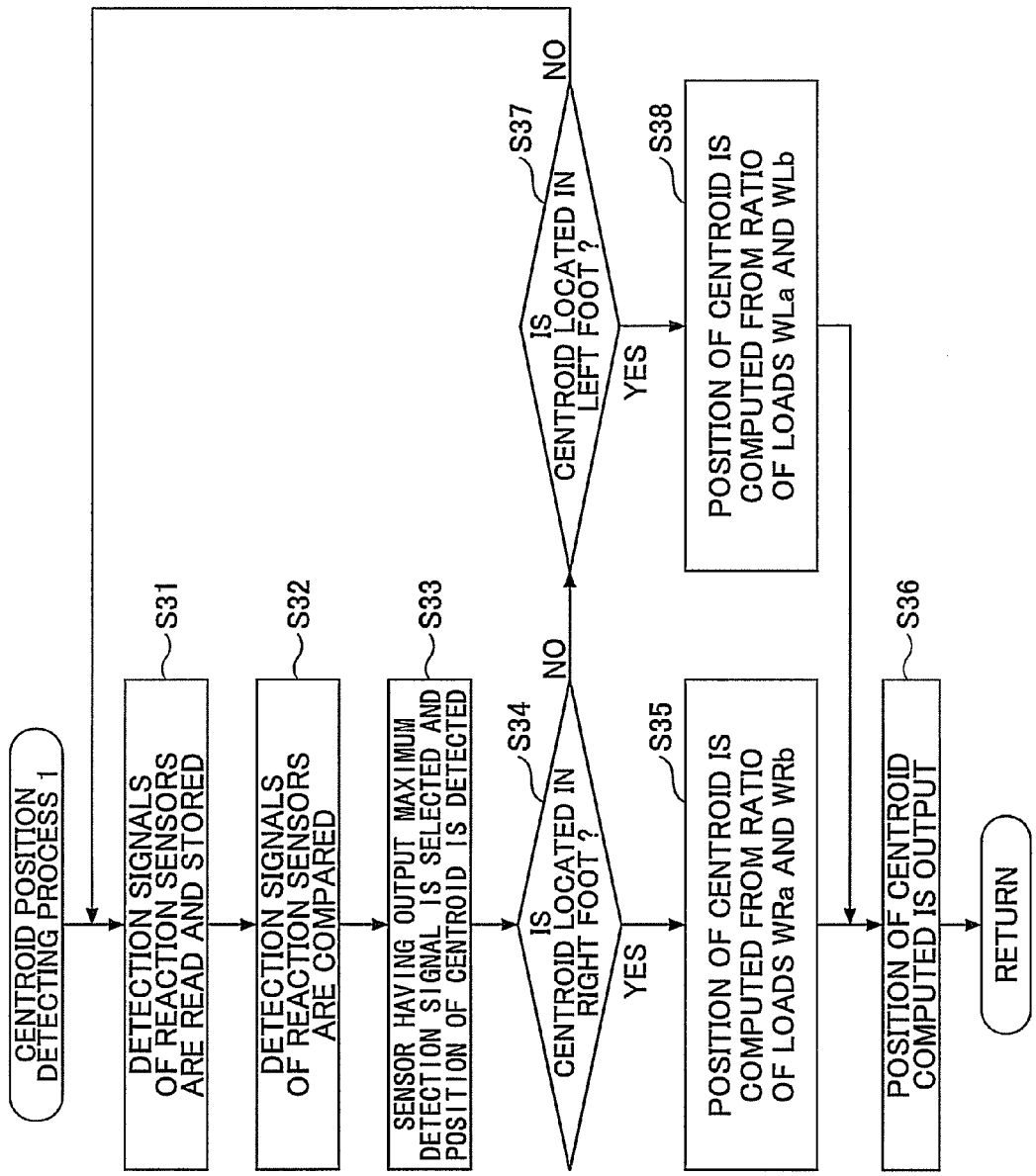
FIG. 13 is a flowchart for explaining a centroid position detection process 1 which is performed by the control device 400 accompanied with a walk action.

As illustrated in FIG. 13, in S31, the control device 400 reads out the detection signals Ra, Rb, La and Lb of the reaction sensors 50a, 50b, 52a and 52b during a walk action (which indicates the capacitance of the capacitor) and stores the detection data in the memory 460.

Subsequently, in S32, the detection signals Ra, Rb, La and Lb of the reaction sensors 50a, 50b, 52a and 52b are compared with each other.

Subsequently, in S33, the reaction sensor that has output the maximum detection signal among the detection signals Ra, Rb, La and Lb is selected from among the reaction sensors 50a, 50b, 52a and 52b. The position of the center of gravity of the wearing person 12 is determined based on the position of the reaction sensor selected in S33 from among the reaction sensors 50a, 50b, 52a and 52b.

Subsequently, it is determined in S34 whether the center of gravity is located in the right foot. When the result of the determination in S34 is affirmative, in S35, the position of the center of gravity on the right foot is computed based on the ratio of the tiptoe load WRa and the heel load WRb detected by the reaction sensors 50a and 50b of the right foot. Subsequently, in S36, the data of the centroid position on the right foot (indicating a distance from the center of the wearing person 12) are output.

When it is determined in S34 that the center of gravity is not located in the right foot, the control progresses to S37. It is determined in S37 whether the center of gravity is located in the left foot. When the result of the determination in S37 is affirmative, in S38, the position of the center of gravity on the left foot is computed based on the ratio of the tiptoe load WLa and the heel load WLb which are measured by the reaction sensors 52a and 52b of the left foot. Subsequently, in S36, the data (indicating a distance from the center of the wearing person 12) of the centroid position of the left foot are output.

When it is determined in S37 that the center of gravity is not located in the left foot, the control is returned to S31 and the subsequent steps are performed again.

As the data of the centroid position, the coordinates of the center position of the wearing person 12 in an X-Y coordinate system may be set to X=0 and Y=0, and the position of the center of gravity (the centroid position) may be expressed by the X directional position and the Y directional position to this reference position.

Next, a centroid position detection process 2 which is performed by the control device 400 accompanied with a walk action of a wearing person will be described with reference to FIG. 14.

In this centroid position detection process 2, a simplified detection method is used in which computation of an accurate position of the center of gravity is not performed and an approximate position of the center of gravity is estimated based on the data of the loads detected by the reaction sensors.

Figure 14:
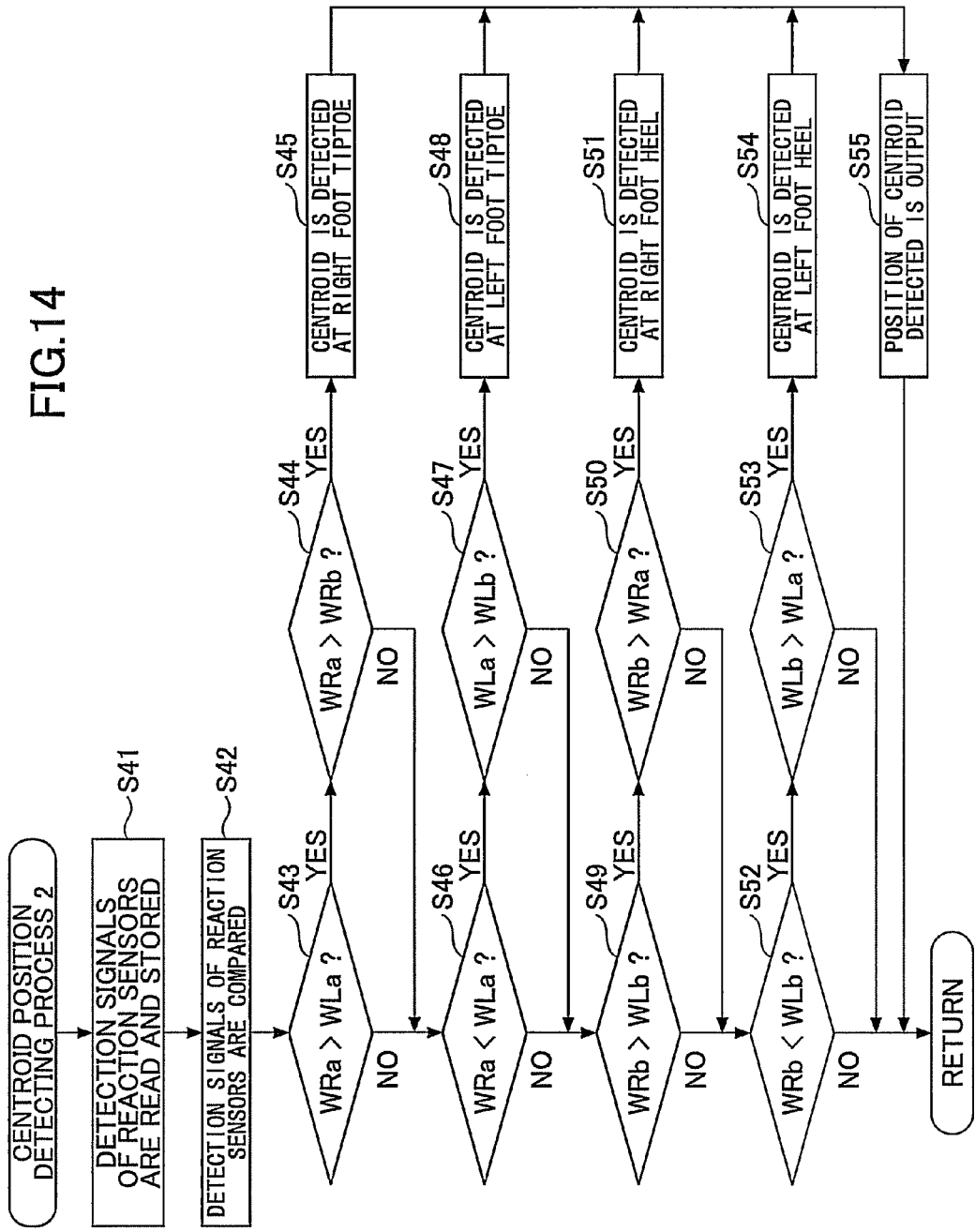
FIG. 14 is a flowchart for explaining a centroid position detection process 2 which is performed by the control device 400 accompanied with a walk action.

As illustrated in FIG. 14, in S41, the control device 400 reads out the detection signals Ra, Rb, La and Lb of the reaction sensors 50a, 50b, 52a and 52b (which indicate the capacitance of the capacitor) and stores the capacitances indicated by the detection signals Ra, Rb, La and Lb in the memory 460.

Subsequently, in S42, the detection signals Ra, Rb, La and Lb of the reaction sensors 50a, 50b, 52a and 52b are compared with each other.

Subsequently, in S43, a load WRa detected by the reaction sensor 50a is compared with a load WLa detected by the reaction sensor 52a, and it is detected in S43 whether the condition WRa>WLa is met. When it is detected in S43 that the condition WRa>WLa is met, the control progresses to S44. In S44, the load WRa detected by the reaction sensor 50a with a load WRb detected by the reaction sensor 52b, and it is detected in S44 whether the condition WRa>WRb is met. When it detected in S44 that the condition WRa>WRb is met, the control progresses to S45. It is determined in S45 that the center of gravity (centroid) is located at the right foot tiptoe. The control progresses to S55. In S55, the result of the determination of the centroid position is output.

When it is detected in S43 the condition WRa>WLa is not met, the control progresses to S46. In S46, the load WRa detected by the reaction sensor 50a is compared with the load WLa detected by the reaction sensor 52a, and it is detected whether the condition WRa<WLa is met. When it is detected in S46 that the condition WRa<WLa is met, the control progresses to S47. In S47, the load WLa detected by the reaction sensor 52a is compared with a load WLb detected by the reaction sensor 52b, and it is detected whether the condition WLa>WLb is met. When it is detected in S47 that the condition WLa>WLb is met, the control progresses to S48. In S48, it is determined that the center of gravity (centroid) is located at the left foot tiptoe. The control progresses to S55. In S55, the result of the determination of the centroid position is output.

When it is detected in S46 that the condition WRa<WLa is not met, the control progresses to S49. In S49, a load WRb detected by the reaction sensor 50b is compared with the load WLb detected by the reaction sensor 52b, and it is detected whether the condition WRb>WLb is met. When it is detected in S49 that the condition WRb>WLb is met, the control progresses to S50. In S50, the load WRa detected by the reaction sensor 50b is compared with the load WRb detected by the reaction sensor 52a, and it is detected whether the condition WRb>WRa is met. When it is detected in S50 that the condition WRb>WRa is met, the control progresses to S51. It is determined in S51 that the center of gravity (centroid) is located at the right foot heel. The control progresses to S55. In S55, the result of the determination of the centroid position is output.

When it is detected in S49 that the condition WRb>WLb is not met, the control progresses to S52. In S52, the load WRb detected by the reaction sensor 50b is compared with the load WLb detected by the reaction sensor 52b, and it is detected whether the condition WRb<WLb is met. When it is detected in S52 that the condition WRb<WLb is met, the control progresses to S53. In S53, the load WLb detected by the reaction sensor 52b is compared with the load WLa detected by the reaction sensor 52a, and it is detected whether the condition WLb>WLa is met. When it is detected in S53 that the condition WLb>WLa is met, the control progresses to S54. It is determined in S54 that the center of gravity (centroid) is located at the left foot heel. The control progresses to S55. In S55, the result of the determination of the centroid position is output.

In the above embodiment, the case in which a shift of the position of the center of gravity during the walk action accompanied with the shift of the weight detected by the reaction sensors 50a, 50b, 52a and 52b is detected has been described. Similarly, detection of the centroid position during another action other than the walk action (for example, detection of the centroid position for a standing position, a standup action of a person who stands up from a chair, or detection of the centroid position accompanied with a stairway rising or falling action) may also be performed.

Next, some modifications of the load measuring parts 50 and 52 will be described.

Figure 15:
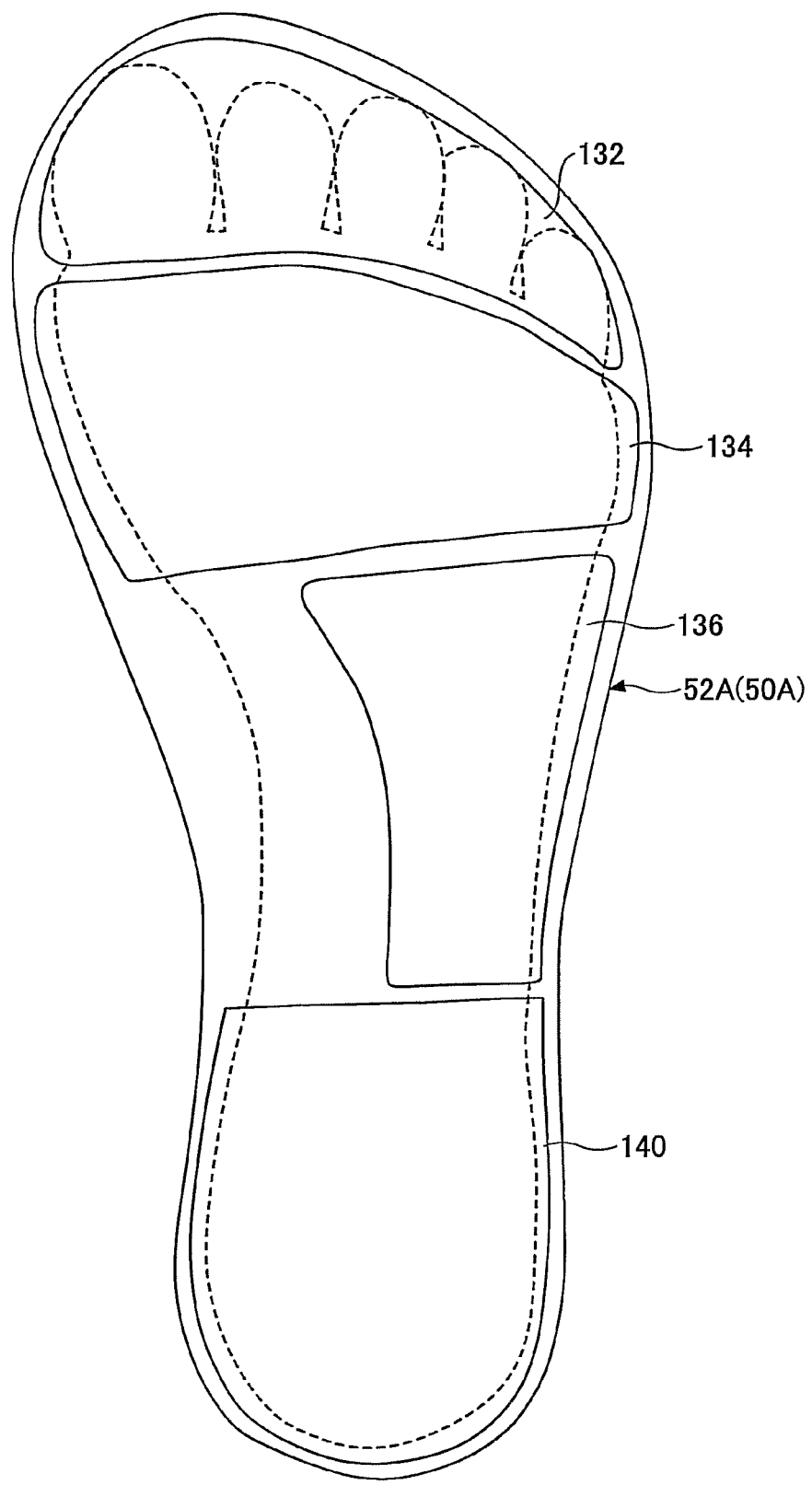
FIG. 15 is a bottom view of a modification 1 of the load measuring part 50 or 52.

FIG. 15 is a bottom view of a modification 1 of the load measuring part 50 or 52. Although FIG. 15 illustrates only the bottom surface of the left foot, the bottom surface of the right foot is arranged in the same manner, and a description thereof will be omitted.

As illustrated in FIG. 15, the load measuring part 50A or 52A of the modification 1 includes a first tiptoe electrode 132, a second tiptoe electrode 134, center-section electrode 136, and a heel electrode 140. Hence, the bottom surface of each foot of the wearing person 12 is divided in the longitudinal direction into four parts, and the load measuring part 50A or 52A detects a capacitance according to the load on each part.

Each of the load measuring parts 50A and 52A of the modification 1 includes four reaction sensors which are formed by the first tiptoe electrode 132, the second tiptoe electrode 134, the center-section electrode 136 and the heel electrode 140. Therefore, it is possible to detect the centroid position on the bottom surfaces of the feet of the wearing person 12 more accurately than in the case of the reaction sensors disposed at the two places, the tiptoe and the heel.

Figure 16:
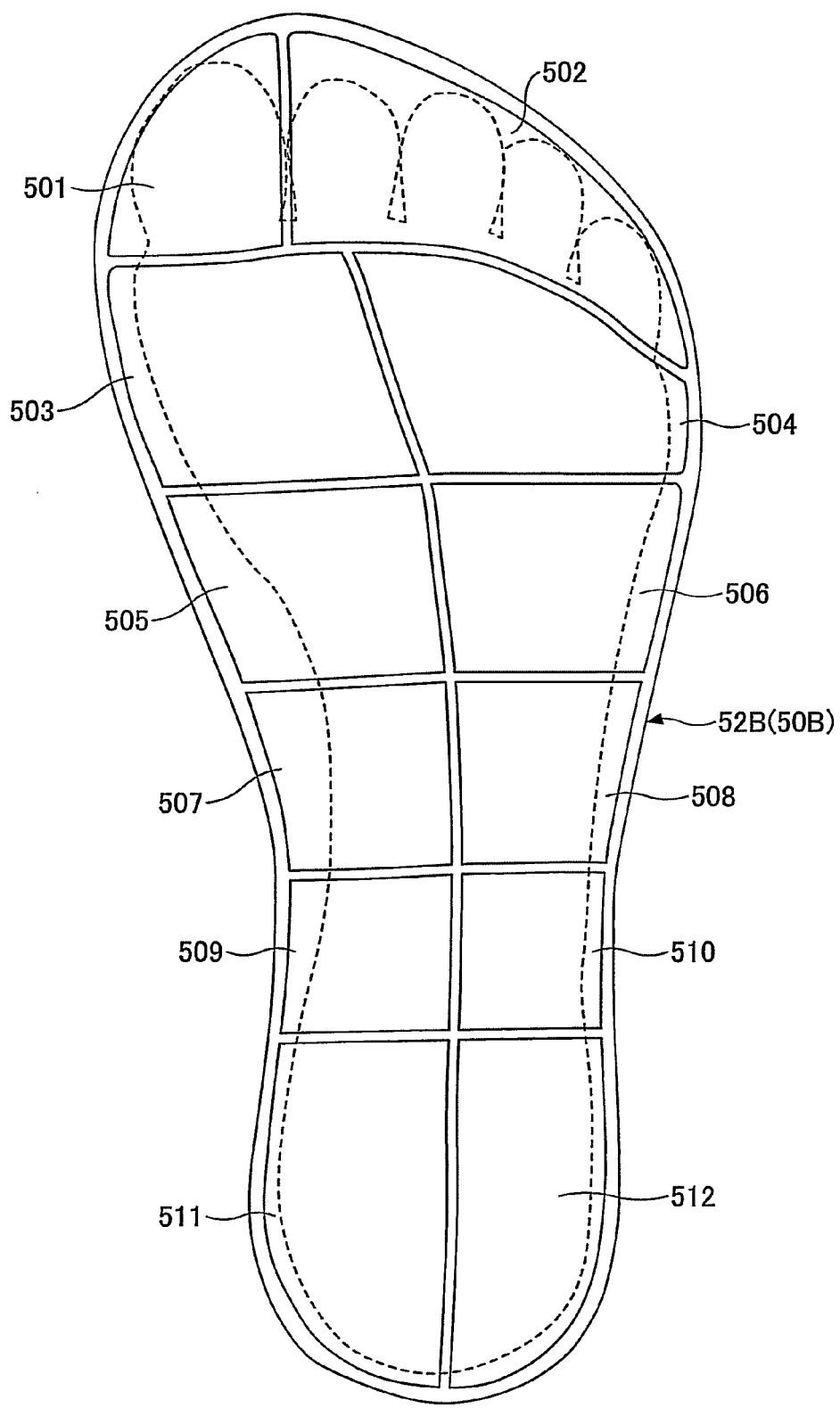
FIG. 16 is a bottom view of a modification 2 of the load measuring part 50 or 52.

FIG. 16 is a bottom view of a modification 2 of the load measuring part 50 or 52. Although FIG. 16 illustrates only the bottom surface of the left foot, the bottom surface of the right foot is arranged in the same manner, and a description thereof will be omitted.

As illustrated in FIG. 16, the bottom surface of each foot of the wearing person 12 is divided into 12 parts, and first to twelfth electrodes 501-512 are arranged at these parts so that the load measuring parts 50B and 52B of the modification 2 can measure the loads at these parts. In this modification 2, the number of electrodes is increased from that in the above-mentioned modification 1, twelve reaction sensors are disposed at the respective parts, and it is possible to detect the centroid position on the bottom surface of each foot of the wearing person 12 more accurately than that of the modification 1.

Figure 17:
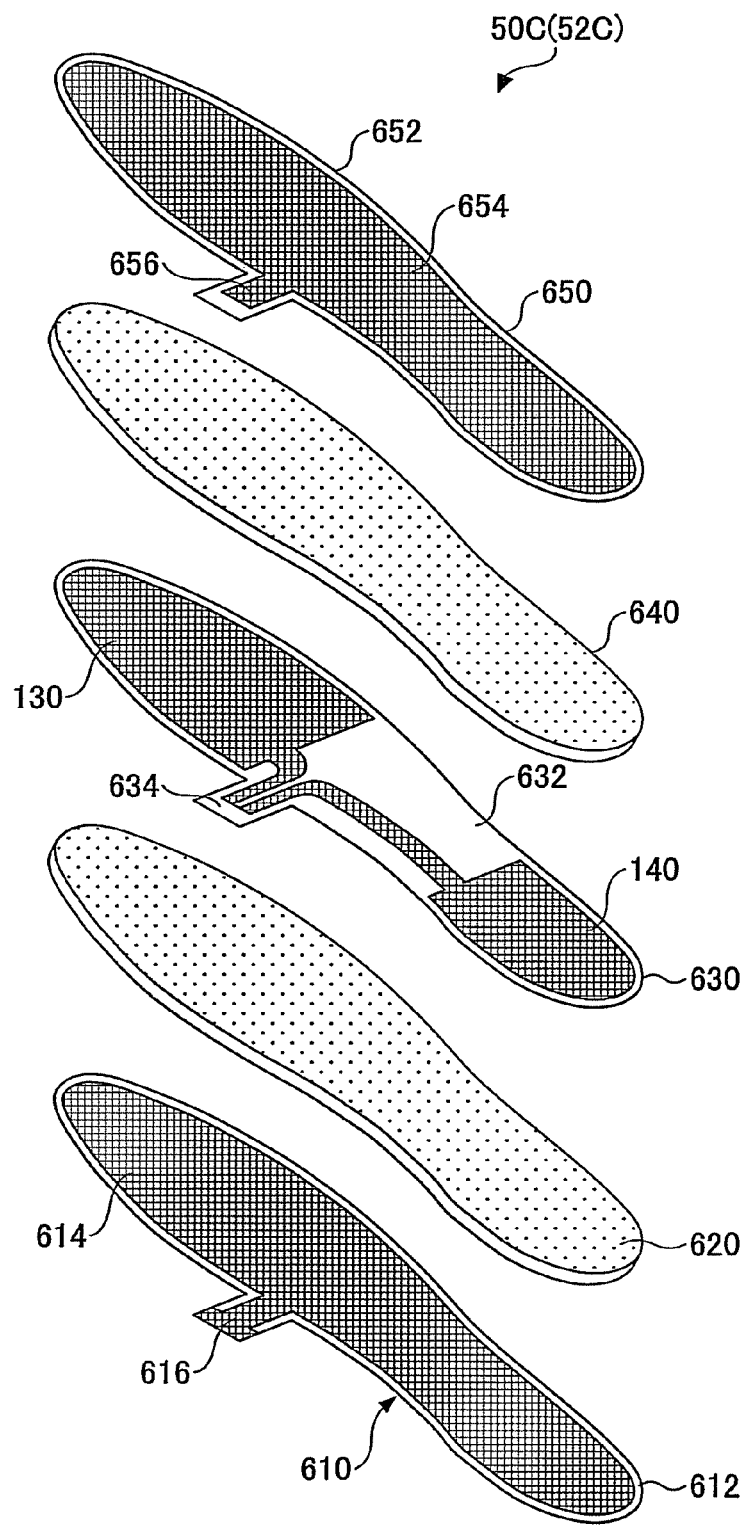
FIG. 17 is an exploded perspective view of a modification 3 of the load measuring part 50 or 52.

FIG. 17 is an exploded perspective view of a modification 3 of the load measuring part 50 or 52. As illustrated in FIG. 17, load measuring parts 50C and 52C of the modification 3 are arranged by a flexible wiring board configuration, and the structure of each load measuring part is constructed by five layers including electrode layers, an insulating layer and an elastic layer, which are laminated on a flexible substrate made of a resin.

Specifically, each of the load measuring parts 50C and 52C includes a lower ground electrode 610, a lower elastic layer 620, an electrode layer 630 in which the tiptoe electrode 130 and the heel electrode 140 are formed, an upper elastic layer 640, and an upper ground electrode 650 which are laminated and bonded together by an adhesive agent.

In the lower ground electrode 610, a net-like electrode pattern 614 (a pattern of wire lines having a diameter smaller than that of the first embodiment) is formed on the top surface of a flexible wiring board 612 of a resin by plating. A connector terminal land 616 which extends transversely is formed at the center portion of the flexible wiring board 612.

The lower elastic layer 620 is formed of a sponge-like elastic material having an insulating characteristic, and has a thickness (about 1 mm) smaller than that of the first embodiment previously described.

In the electrode layer 630, a net-like electrode pattern (a pattern of wire lines having a diameter smaller than that of the first embodiment) as the tiptoe electrode 130 and the heel electrode 140 is formed on the top surface of the flexible wiring board 632 by plating. A connector terminal land 634 which extends transversely is formed at the center portion of the flexible wiring board 632.

Similar to the lower elastic layer 620, the upper elastic layer 640 is formed of a sponge-like elastic material having an insulating characteristic and has a thickness (about 1 mm) smaller than that of the first embodiment previously described.

Similar to the lower ground electrode 610, in the upper ground electrode 650, a net-like electrode pattern 654 (a pattern of wire lines having a diameter smaller than that of the first embodiment) is formed on the bottom surface of the flexible wiring board 652 of a resin by plating. A connector terminal land 656 which extends transversely is formed at the center portion of the flexible wiring board 652.

In this manner, the load measuring parts 50C and 52C are arranged so that the above-described flexible wiring boards 612, 632 and 652 are laminated, and have a thickness smaller than that of the first embodiment. Moreover, in the load measuring parts 50C and 52C, the electrode patterns are formed on the flexible wiring boards 612, 632 and 652 which are capable of absorbing elastic deformation, and interposed between the elastic layers 620 and 640 in the vertical direction. It is possible to prevent open-circuiting of the wires over an extended period of use.

The thicknesses and materials of the lower elastic layer 620 and the upper elastic layer 640 are not restricted to the above-described examples. Arbitrary thicknesses and materials may be selected depending on the use conditions, such as the weight of the wearing person 12 weight or the frequency of use, and the load measuring parts 50C and 52C suitable for the wearing person 12 may be provided.

Similar to the first embodiment previously described, the load measuring parts 50C and 52C of the modification 3 are arranged so that the tiptoe electrode 130 and the heel electrode 140, and the upper ground electrode 650 and the lower ground electrode 610 may constitute the capacitor C and a capacitance of the capacitor C according to the load can be detected. Therefore, if the load acts accompanied with a walk action of the wearing person 12, the lower elastic layer 620 and the upper elastic layer 640 are compressed, the distance between the electrodes is changed, and the detected capacitance is changed. Thereby, with the load measuring parts 50C and 52C of the modification 3, it is possible to accurately detect the centroid position accompanied by a walk action of the wearing person 12.

The flexible wiring boards 652 and 612 are formed on the top surface and the bottom surface of the load measuring parts 50C and 52C. Hence, coating of the load measuring parts 50C and 52C with an insulating material, after the lamination, may be omitted. It is possible to decrease the number of manufacturing steps.

Figure 18:
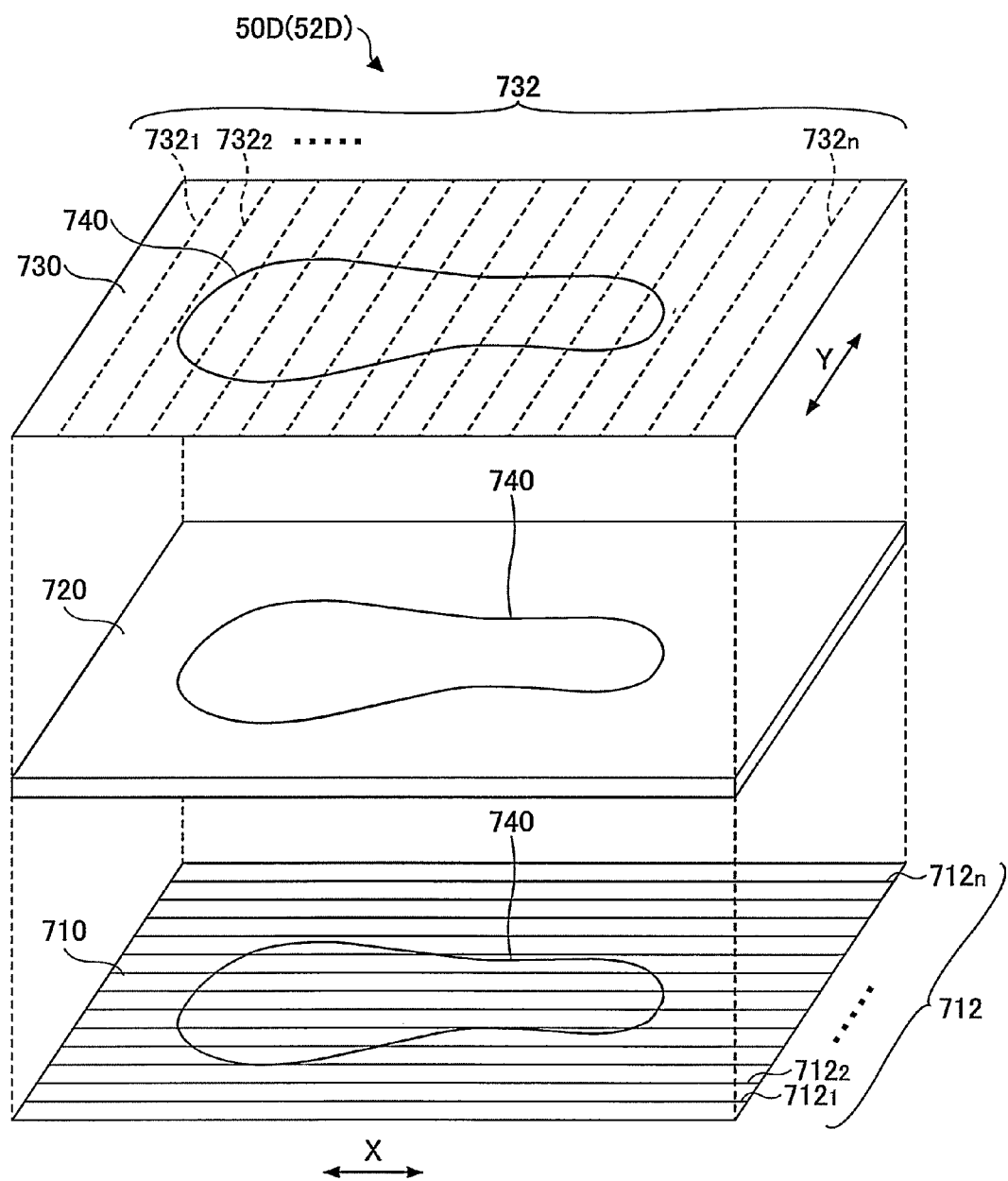
FIG. 18 is an exploded perspective view of a modification 4 of the load measuring part 50 or 52.

FIG. 18 is an exploded perspective view of a modification 4 of the load measuring part 50 or 52. As illustrated in FIG. 18, the load measuring part 50D or 52D of the modification 4 is arranged so that a lower electrode sheet (first electrode sheet) 710, an elastic sheet (elastic plate) 720, and an upper electrode sheet (second electrode sheet) 730 are laminated in a vertical direction and bonded together by an adhesive agent.

In the lower electrode sheet 710, a plurality of electrode wires 712 ($712_1$-$712_n$) extending in the direction X are arranged in parallel with the direction X at a given spacing. The lower electrode sheet 710 is formed of a film-like flexible substrate of an insulating material having a flexibility, and this lower electrode sheet 710 has a thickness of about 0.5 mm, for example.

As a method of fixing the electrode wires 712, molding may be performed so that the electrode wires 712 are embedded on the surface or the core of the lower electrode sheet 710, or a thin film fabrication method, such as an electroplating method, a vapor-depositing method or a spattering method may be performed to form a pattern of thin electrodes on the surface of the lower electrode sheet 710.

For example, the elastic sheet 720 is formed from a sponge-like elastic plate having an insulating characteristic, and has a very small thickness (about 1 mm) which is smaller than that of the embodiment 1 described above.

In the upper electrode sheet 730, a plurality of electrode wires 732 ($732_1$-$732_n$) extending in the direction Y which is perpendicular to the extending direction of the electrode wires 712 of the lower electrode sheet 710 are arranged in parallel with the direction Y at a given spacing. Similar to the lower electrode sheet 710 described above, the upper electrode sheet 730 is formed of a film-like flexible substrate of an insulating material having a flexibility, and this upper electrode sheet 730 has a thickness of about 0.5 mm, for example. The electrode wires 732 may be arranged by the same method as the electrode wires 712.

The spacing of the electrode wires 712 or 32 may be set up to an arbitrary distance. For example, when the thickness of the core of the electrode wires 712 or 732 is in a range of 0.1-0.3 mm, the spacing of the electrode wires 712 or 732 may be set up to be in a range of 1-3 mm.

After the lower electrode sheet 710, the elastic sheet (elastic layer) 720, and the upper electrode sheet 730 are laminated in the vertical direction, the laminated sheet is cut into a configuration according to the outline of a footprint 740 of the wearing person 12. In the laminated condition in which the elastic sheet 720 is sandwiched between the lower electrode sheet 710 and the upper electrode sheet 730, the lower electrode sheet 710, the elastic sheet 720, and the upper electrode sheet 730 are bonded together. Each wire of a flexible cable is connected to each of the electrode wires 712 and 732 so that electrical connection of each wire is made.

The load measuring parts 500 and 520 are arranged so that the lower electrode sheet 710 and the upper electrode sheet 730, which are made of a film-like resin material, are laminated and bonded on the bottom surface and the top surface of the elastic sheet 720, respectively, and the load measuring parts 500 and 52D are flexibly expanded and contracted according to a change of the load accompanied with a shift of the weight of the wearing person during a walk action. Therefore, the impact on the wearing person 12 during a walk action can be eased, and open circuiting of the electrode wires 712 and 732 can be prevented. The walk action of the wearing person 12 can be assisted without giving a sense of incongruity.

One method of bonding the load measuring parts 500 and 52D is that an adhesive agent is applied to the interfaces between the lower electrode sheet 710, the elastic sheet 720 and the upper electrode sheet 730, and they are pressurized in the vertical direction and bonded together. Another bonding method is that high-frequency heating is applied to the peripheral parts of the lower electrode sheet 710 and the upper electrode sheet 730 corresponding to the outline of the footprint 740, the peripheral parts are locally heated and fused, and the peripheral parts are bonded together through the fused heating.

In the load measuring parts 50D and 52D, the elastic sheet 720 is interposed between the lower electrode sheet 710 and the upper electrode sheet 730, and the lower electrode sheet 710, the elastic sheet 720 and the upper electrode sheet 730 are laminated. The electrode wires 712 ($712_1$-$712_n$) extending in the direction X and the electrode wires 732 ($732_1$-$732_n$) extending in the direction Y are arranged to form a matrix of rows and columns, and each of the intersections between the electrode wires 712 ($712_1$-$712_n$) and the electrode wires 732 ($732_1$-$732_n$) forms a capacitor. Therefore, one of the electrode wires 712 ($712_1$-$712_n$) and the electrode wires 732 ($732_1$-$732_n$) are connected to the constant-voltage power source and the other are grounded (on the ground side). By measuring a capacitance at each of the intersections sequentially, it is possible to measure a distribution of loads on the whole sole surface of the wearing person 12.

A number of load measuring parts with different sizes in which the lower electrode sheet 710, the elastic sheet 720 and the upper electrode sheet 730 are laminated and bonded may be prepared beforehand. In such a case, if the outline of footprints of a wearing person 12 is measured, it is possible to efficiently manufacture the load measuring parts 50D and 52D that are suitable for the size of the feet of the wearing person 12.

For example, electric conduction of each of the electrode wires 712 and 732 may be made by switching of a selector switch. Alternatively, the timing of electric conduction of each of the electrode wires 712 and 732 may be switched at intervals of 0.05-0.2 seconds by using the control by the software. If a rate of change of a capacitance (which is determined by the gradient angle of the graph illustrated in FIG. 7) at the intersecting point of the activated electrode wire 712 and the electrode 732 facing the activated electrode wire 712 is detected instantaneously, it is possible to efficiently detect the capacitances of all the intersecting points of the electrode wires 712 and 732.

With the load measuring parts 500 and 520, the capacitances of 50-100 points (intersections) on the sole side of a wearing person can be detected, and measurement of the loads at the respective points is possible. Hence, it is possible to accurately measure a distribution of the loads on the back surfaces of the right and left feet of the wearing person 12 accompanied with a walk action of the wearing person 12. For example, when a wearing person 12 who wears the action assistance device 10 walks for the first time, the measurement and storage of the data covering the habitual walk action specific to the wearing person 12, and positional deviations of the center of gravity (changes of the right, left, front and rear loads) can be easily performed for each individual person. By using the accumulated data obtained through the measurement and storage, simulation of the walk action, inclination conditions, deviations of the forward direction, etc. by the wearing person 12 who wears the action assistance device 10 can be performed on the computer display.

As a modification of the load measuring parts 50D and 52D, a plurality of electrode wires 712 and a plurality of electrode wires 732 may be fabricated directly on the bottom surface and the top surface of an elastic sheet 720, and a resin film having an insulating characteristic may be fabricated on the top and bottom surfaces of the elastic sheet 720 and the surface of the electrode wires 712 and 732.

This international application is based on and claims the benefit of priority of Japanese patent application No. 2007-337166, filed on Dec. 27, 2007, the contents of which are incorporated herein by reference in their entirety.

The invention claimed is:

1. A centroid position detector device, comprising:
   a load measuring part fitted in contact with a sole side of a foot of a person and configured to measure a value of a load on the sole side of the foot of the person based on a capacitance that varies according to a shift of a weight of the person; and
   a centroid detecting unit configured to detect a position of a center of gravity of the person based on a change in the load value measured based on the capacitance by the load measuring part,
   wherein the load measuring part includes
      a sheet-like elastic plate having elasticity,
      an upper electrode bonded to a top surface of the elastic plate, and
      a lower electrode bonded to a bottom surface of the elastic plate;
   wherein the load measuring part is arranged to detect a capacitance between the upper electrode and the lower electrode; and
   wherein one of the upper and lower electrodes is grounded, the other of the upper and lower electrodes is connected to a constant-voltage power source, and the capacitance is computed based on a time taken by a value of a voltage between the upper electrode and the lower electrode to reach a predetermined value.

2. The centroid position detector device according to claim 1, wherein the load measuring part is arranged to measure loads at two positions, corresponding to a tiptoe and a heel, on the sole side of the foot.

3. The centroid position detector device according to claim 1, wherein the load measuring part is arranged in an insole of a shoe.

4. A centroid position detector device, comprising:
a load measuring part fitted in contact with a sole side of a foot of a person and configured to measure a value of a load on the sole side of the foot of the person based on a capacitance that varies according to a shift of a weight of the person; and
a centroid detecting unit configured to detect a position of a center of gravity of the person based on a change in the load value measured based on the capacitance by the load measuring part,
wherein the load measuring part comprises:
a lower ground electrode,
a lower elastic plate laminated on a top surface of the lower ground electrode,
a voltage sensing electrode laminated on a top surface of the lower elastic plate,
an upper elastic plate laminated on a top surface of the voltage sensing electrode, and
an upper ground electrode laminated on a top surface of the upper elastic plate;
wherein the load measuring part is arranged to detect a capacitance based on a time taken by a voltage detected from the voltage sensing electrode to reach a predetermined reference voltage.

5. The centroid position detector device according to claim 4, wherein the load measuring part is arranged so that the lower ground electrode, the lower elastic plate, the voltage sensing electrode, the upper elastic plate, and the upper ground electrode are laminated and bonded together.

6. The centroid position detector device according to claim 1, wherein the load measuring part comprises:
a first electrode sheet having a plurality of electrode wires arranged in parallel with a first direction at intervals of a predetermined distance;
an elastic sheet laminated on a top surface of the first electrode sheet; and
a second electrode sheet laminated on a top surface of the elastic sheet and having a plurality of electrode wires arranged in parallel with a second direction at intervals of a predetermined distance, the second direction being not parallel to the first direction,
wherein a capacitance is sequentially detected at each of a plurality of points where the electrode wires of the first electrode sheet and the electrode wires of the second electrode sheet intersect each other.

7. The centroid position detector device according to claim 6, wherein the first electrode sheet and the second electrode sheet are formed of a film-like flexible substrate, the elastic sheet is interposed between the first electrode sheet and the second electrode sheet, and the first electrode sheet, the elastic sheet, and the second electrode sheet are laminated and bonded together.

8. A wearing type action assistance device, comprising:
the centroid position detector device according to claim 1;
an actuator to generate an action assisting force;
a frame to transmit a driving force of the actuator to the foot of the wearing person;
a biosignal detecting part to detect a biosignal from the wearing person accompanied with a walk action of the wearing person; and
a control unit to control the driving force of the actuator based on the biosignal detected by the biosignal detecting part and the position of the center of gravity detected by the centroid position detector device.

9. The wearing type action assistance device according to claim 8, wherein the load measuring part includes:
a first load measuring part to measure a right foot load acting on a bottom surface of a right foot of the wearing person; and
a second load measuring part to measure a left foot load acting on a bottom surface of a left foot of the wearing person, and
wherein the centroid detecting unit detects a position of the center of gravity of the wearing person based on a rate of the right foot load measured by the first load measuring part and the left foot load measured by the second load measuring part.

10. The centroid position detector device according to claim 1, wherein-the load measuring part includes:
a first load measuring part to measure a right foot load acting on a bottom surface of a right foot of the wearing person; and
a second load measuring part to measure a left foot load acting on a bottom surface of a left foot of the wearing person.

* * * * *